United States Patent
Shmueli

(10) Patent No.: US 11,298,169 B2
(45) Date of Patent: Apr. 12, 2022

(54) BONE ANCHOR, KIT AND METHOD OF USE

(71) Applicant: Gad Shmueli, Yad Natan (IL)

(72) Inventor: Gad Shmueli, Yad Natan (IL)

( * ) Notice: Subject to any disclaimer, the term of this patent is extended or adjusted under 35 U.S.C. 154(b) by 34 days.

(21) Appl. No.: 16/630,506

(22) PCT Filed: Jul. 12, 2018

(86) PCT No.: PCT/IL2018/050768
§ 371 (c)(1),
(2) Date: Jan. 13, 2020

(87) PCT Pub. No.: WO2019/012540
PCT Pub. Date: Jan. 17, 2019

(65) Prior Publication Data
US 2020/0163704 A1    May 28, 2020

Related U.S. Application Data

(60) Provisional application No. 62/531,399, filed on Jul. 12, 2017.

(51) Int. Cl.
*A61B 17/86*    (2006.01)
*A61B 17/17*    (2006.01)
(Continued)

(52) U.S. Cl.
CPC .......... *A61B 17/8635* (2013.01); *A61B 17/17* (2013.01); *A61B 2017/044* (2013.01); *A61C 8/0024* (2013.01); *A61F 2002/0829* (2013.01)

(58) Field of Classification Search
CPC ... A61B 17/86; A61B 17/8605; A61B 17/861; A61B 17/8615; A61B 17/862;
(Continued)

(56) References Cited

U.S. PATENT DOCUMENTS

| 1,465,148 | A | * | 8/1923 | Rosenberg | .......... F16B 25/0031 |
| | | | | | 411/418 |
| 1,933,332 | A | * | 10/1933 | May | .......... F16B 39/30 |
| | | | | | 411/418 |

(Continued)

FOREIGN PATENT DOCUMENTS

| CH | 693733 | 1/2004 |
| CN | 104717932 A | 6/2015 |

(Continued)

OTHER PUBLICATIONS

International Search Report and Written Opinion of the Searching Authority, International Application No. PCT/IL2018/050768, dated Oct. 22, 2018.

(Continued)

*Primary Examiner* — Eric S Gibson
(74) *Attorney, Agent, or Firm* — The Roy Gross Law Firm, LLC; Roy Gross

(57) ABSTRACT

According to an aspect of some embodiments there is provided a bone anchor including an elongated core having a tip at a distal end and coupled to a head at a proximal end, and a segmented helical thread defining one or more gaps therein, each gap defining at least a trailing wall, the trailing wall having a cutting surface including at least one cutting edge. The bone cutting surface and the cutting edge configured to cut bone and guide bone fragments radially inwards. According to an aspect of some embodiments there is further provided a bone anchor kit and a method for implanting the bone anchor in bone.

16 Claims, 16 Drawing Sheets

(51) Int. Cl.
*A61B 17/04* (2006.01)
*A61C 8/00* (2006.01)
*A61F 2/08* (2006.01)

(58) Field of Classification Search
CPC .............. A61B 17/8625; A61B 17/863; A61B 17/8635; A61B 17/864; A61B 17/8645
See application file for complete search history.

(56) References Cited

U.S. PATENT DOCUMENTS

| | | | |
|---|---|---|---|
| 2,093,172 A | 9/1937 | Olson | |
| 2,269,708 A | 1/1942 | Dickson | |
| 3,426,642 A | 2/1969 | Phipard, Jr. | |
| 3,466,478 A | 9/1969 | Gail | |
| 3,672,058 A | 6/1972 | Nikoghossian | |
| 3,987,698 A | 10/1976 | Rabe | |
| 4,177,524 A | 12/1979 | Grell et al. | |
| 4,425,066 A | 1/1984 | Kollmann | |
| 4,466,314 A | 8/1984 | Rich | |
| 4,513,300 A | 4/1985 | Tatsuno et al. | |
| 4,653,486 A | 3/1987 | Coker | |
| 4,815,909 A | 3/1989 | Simons | |
| 5,110,245 A * | 5/1992 | Hiroyuki | F16B 25/0015 411/417 |
| 5,282,863 A | 2/1994 | Burton | |
| 5,578,034 A | 11/1996 | Estes | |
| 5,716,358 A | 2/1998 | Ochoa et al. | |
| 6,001,104 A | 12/1999 | Benderev et al. | |
| 6,022,177 A | 2/2000 | Hofer | |
| 6,048,204 A | 4/2000 | Klardie et al. | |
| 6,428,317 B1 | 8/2002 | Abel | |
| 6,575,975 B2 | 6/2003 | Brace et al. | |
| 6,676,352 B2 * | 1/2004 | Chen-Chi | F16B 37/125 411/178 |
| 7,063,491 B2 * | 6/2006 | French | F16B 15/06 411/387.1 |
| 7,156,600 B2 | 1/2007 | Panasik et al. | |
| 7,699,881 B2 * | 4/2010 | Willmann | A61B 17/863 606/309 |
| 8,128,671 B2 * | 3/2012 | Taylor | A61B 17/863 606/315 |
| 8,292,932 B2 | 10/2012 | Matthis et al. | |
| 8,635,894 B2 | 1/2014 | Christ | |
| 9,526,547 B2 * | 12/2016 | Reed | A61B 17/864 |
| 9,782,209 B2 * | 10/2017 | Reed | A61B 17/8625 |
| 9,949,776 B2 * | 4/2018 | Mobasser | A61B 17/8635 |
| 9,962,240 B2 * | 5/2018 | Park | A61C 8/0022 |
| 10,085,782 B2 * | 10/2018 | Reed | A61B 17/863 |
| 10,136,902 B2 * | 11/2018 | Farris | A61B 17/1655 |
| 11,000,326 B1 * | 5/2021 | Alon | A61B 17/8625 |
| 2004/0121289 A1 * | 6/2004 | Miller | A61C 8/0022 433/174 |
| 2004/0253076 A1 * | 12/2004 | French | F16B 25/0068 411/417 |
| 2005/0019731 A1 | 1/2005 | Björn et al. | |
| 2005/0175432 A1 * | 8/2005 | Su | F16B 25/10 411/417 |
| 2005/0187555 A1 | 8/2005 | Biedermann et al. | |
| 2006/0285940 A1 * | 12/2006 | Walther | F16B 25/0073 411/421 |
| 2007/0043372 A1 * | 2/2007 | Willmann | A61B 17/863 606/264 |
| 2007/0122764 A1 | 5/2007 | Balfour et al. | |
| 2008/0249579 A1 * | 10/2008 | Taylor | A61B 17/863 606/317 |
| 2009/0222103 A1 | 9/2009 | Fitz et al. | |
| 2011/0070558 A1 * | 3/2011 | Park | A61C 8/0025 433/174 |
| 2011/0098756 A1 * | 4/2011 | Brannon | A61B 17/8625 606/309 |
| 2012/0109216 A1 | 5/2012 | Austin et al. | |
| 2012/0136398 A1 * | 5/2012 | Mobasser | A61B 17/8635 606/311 |
| 2013/0022942 A1 * | 1/2013 | Zadeh | A61C 8/006 433/174 |
| 2013/0089835 A1 | 4/2013 | Jensen | |
| 2013/0253649 A1 * | 9/2013 | Davis | A61F 2/446 623/17.16 |
| 2013/0337410 A1 | 12/2013 | Ten Bruggenkate | |
| 2014/0023990 A1 * | 1/2014 | Zadeh | A61C 8/0024 433/174 |
| 2014/0094859 A1 * | 4/2014 | Reed | A61B 17/8625 606/312 |
| 2014/0243912 A1 * | 8/2014 | Mobasser | A61B 17/863 606/311 |
| 2014/0257409 A1 * | 9/2014 | Reed | A61B 17/8625 606/304 |
| 2015/0086942 A1 * | 3/2015 | Hwang | A61C 8/0075 433/174 |
| 2016/0256209 A1 * | 9/2016 | Mobasser | A61B 17/8635 |
| 2017/0119444 A1 * | 5/2017 | Reed | A61B 17/863 |
| 2017/0196611 A1 | 7/2017 | Shmueli | |
| 2019/0290341 A1 * | 9/2019 | Loftus | A61B 17/8625 |
| 2019/0350600 A1 * | 11/2019 | Lehman, Jr | A61B 17/7077 |
| 2019/0388131 A1 * | 12/2019 | Mehl | A61B 17/864 |
| 2020/0163704 A1 * | 5/2020 | Shmueli | A61C 8/0022 |
| 2020/0323574 A1 * | 10/2020 | Picha | A61B 17/864 |
| 2021/0153911 A1 * | 5/2021 | Stuart | A61B 17/863 |

FOREIGN PATENT DOCUMENTS

| | | |
|---|---|---|
| WO | 2015186123 | 12/2015 |
| WO | 2019012540 | 1/2019 |

OTHER PUBLICATIONS

International Preliminary Report on Patentability, International Application No. PCT/IL2018/050768, dated Jan. 23, 2020.
International Search Report and Written Opinion of the Searching Authority, International Application No. PCT/IL2015/050486, dated Oct. 7, 2015.
International Preliminary Report on Patentability, International Application No. PCT/IL2015/050486, dated Dec. 15, 2016.
U.S. Appl. No. 62/006,186, dated Jun. 1, 2014.
United States Office Action, U.S. Appl. No. 15/314,533, dated Mar. 25, 2019.
United States Office Action, U.S. Appl. No. 15/314,533, dated Sep. 24, 2019.
Notice of Allowance, U.S. Appl. No. 15/314,533, dated Feb. 5, 2020.
Search Report of EP Application No. 18832130.1 dated Feb. 18, 2021; 12 pp.
Office Action of Chinese Patent Application No. 201880055352.3; dated Mar. 15, 2021; 10 pp.

* cited by examiner

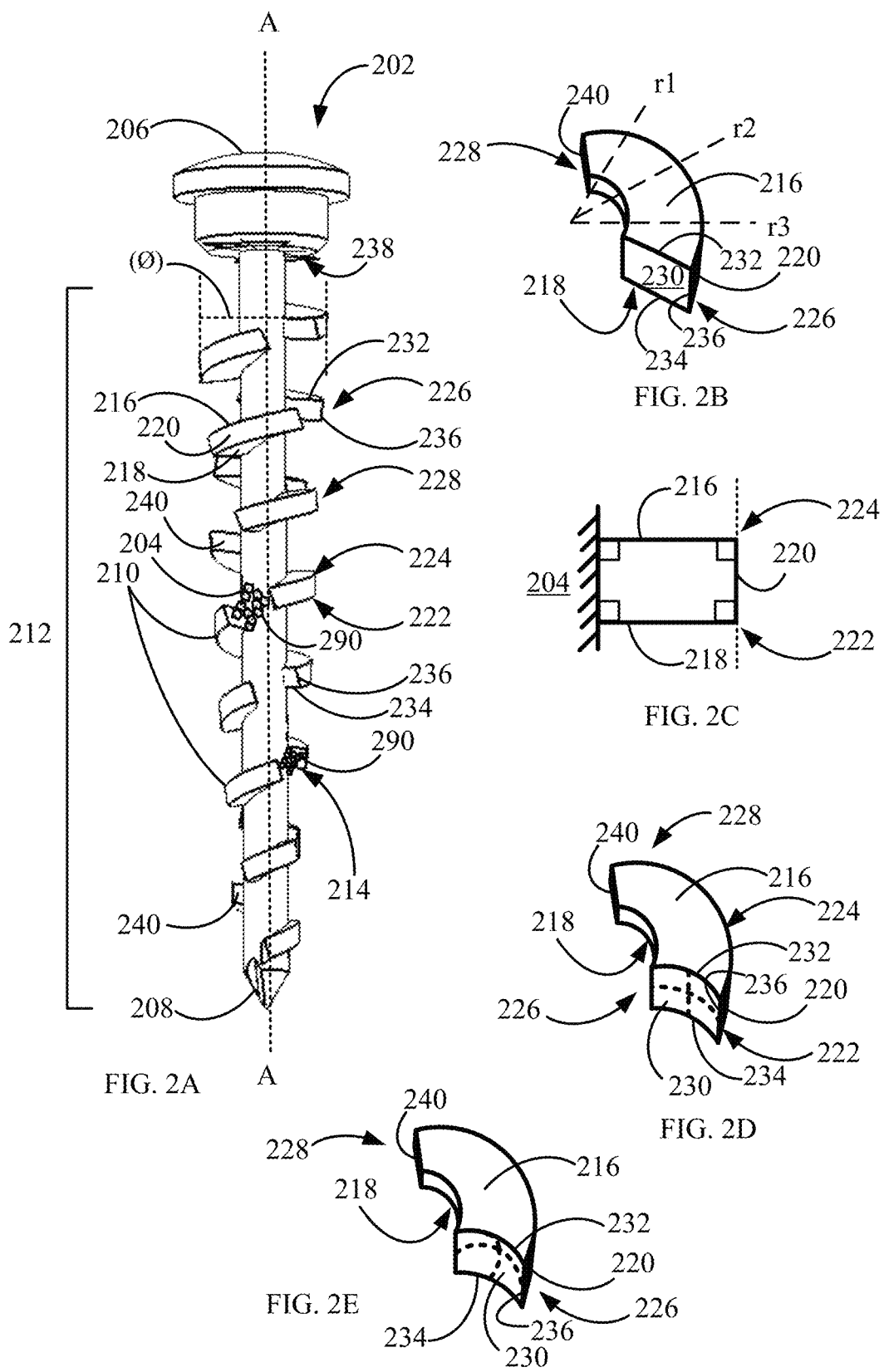

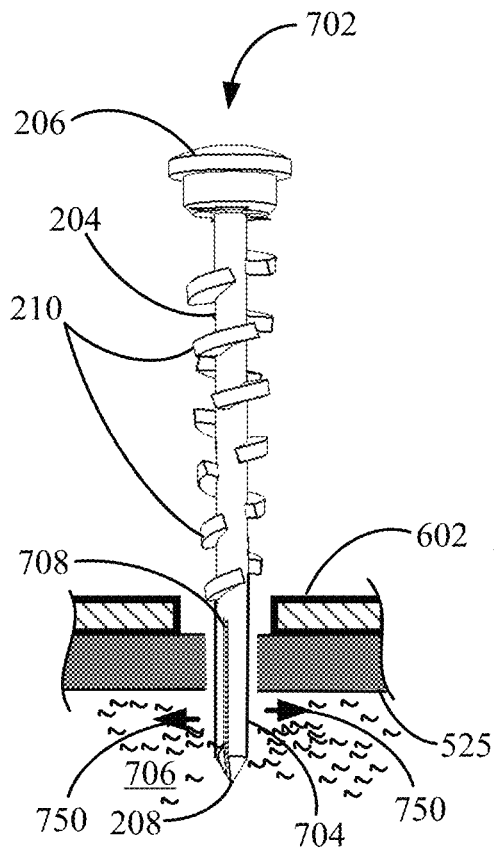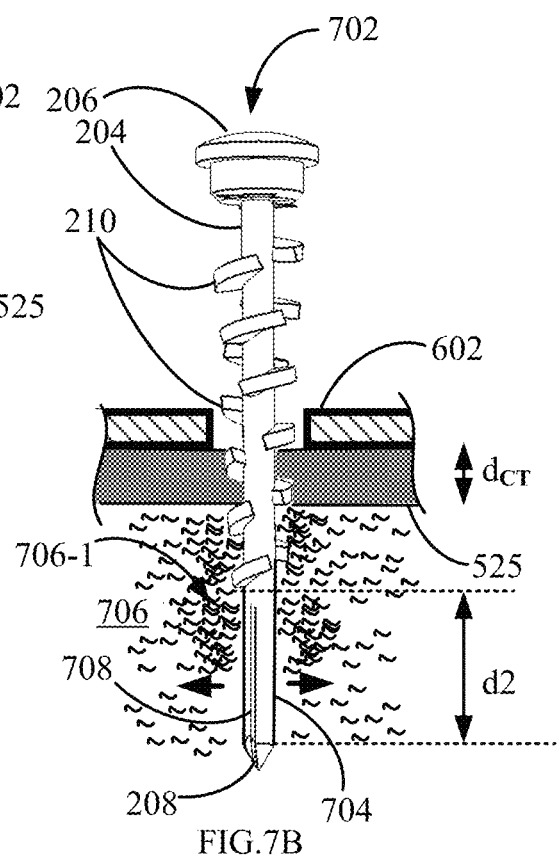
FIG.7A
FIG.7B

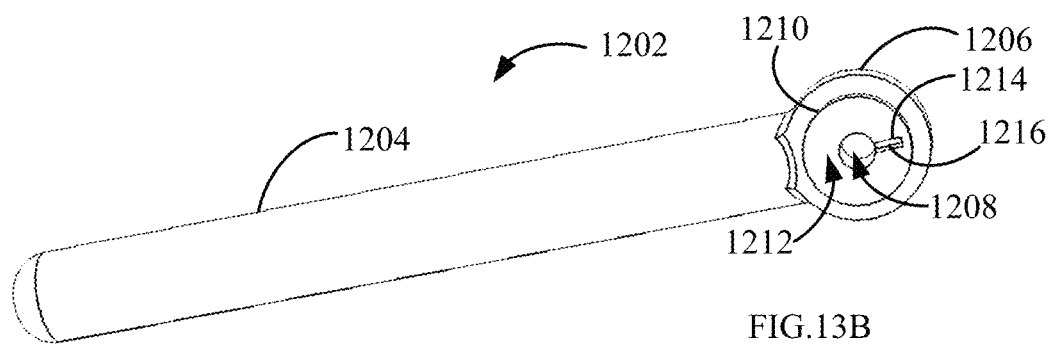
FIG.13B
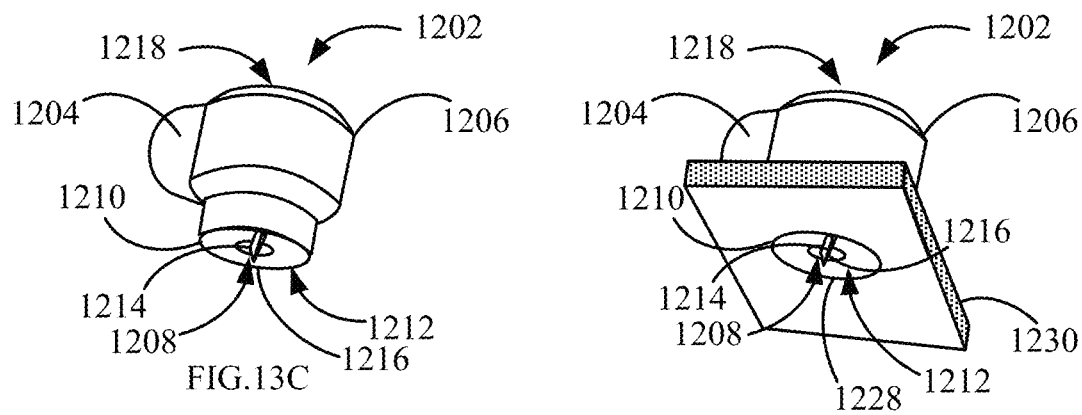
FIG.13C
FIG.13D
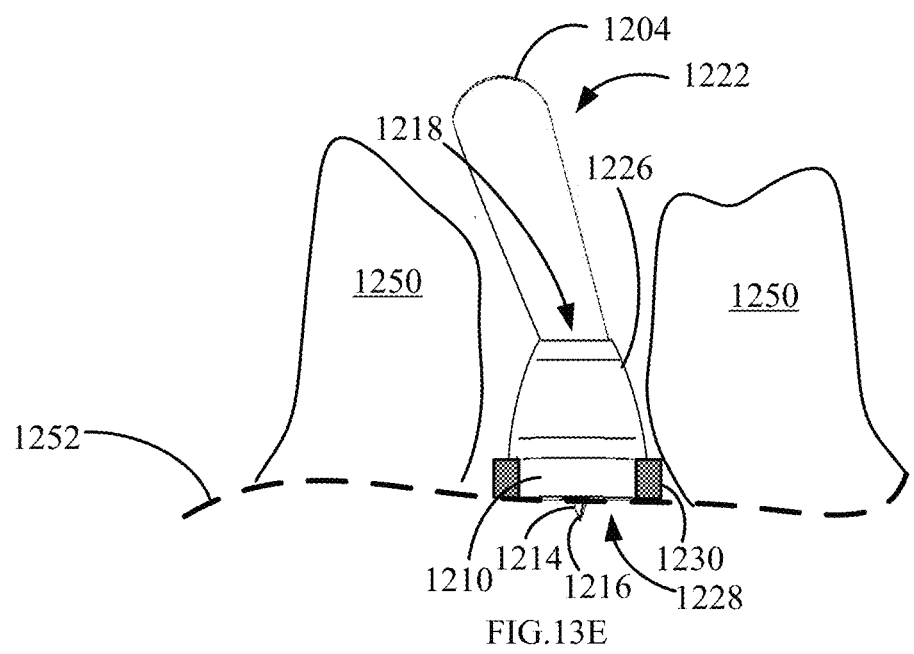
FIG.13E

BONE ANCHOR, KIT AND METHOD OF USE

CROSS-REFERENCE TO RELATED APPLICATIONS

This application is a National Phase of PCT Patent Application No. PCT/IL2018/050768 having International filing date of Jul. 12, 2018 titled "BONE ANCHOR KIT AND METHOD OF USE", which claims the benefit of priority of U.S. Provisional Patent Application No. 62/531,399, filed Jan. 12, 2017 titled "BONE ANCHOR AND METHOD OF USE", the contents of the above applications are all incorporated by reference as if fully set forth herein in their entirely.

FIELD AND BACKGROUND OF THE INVENTION

The present invention, in some embodiments thereof, relates to bone anchors and, more particularly, but not exclusively, to self-tapping bone anchors.

Fixation devices such as screws, pins or similar are commonly used to fix implants and support devices (e.g., bone plates) to bone and may also be used alone, as implants, around joints to hold cancellous bone fragments together e.g., in compound fractures.

Commonly such fixation devices may be subject to high stress such as compression and shearing forces, bending forces, torque or a combination of all resulting from a shift of load-bearing articulating surfaces during movement of the articulating bones such as during walking or in load bearing surfaces e.g., on a tooth implant while chewing, bringing about loosening of the fixation device.

SUMMARY OF THE INVENTION

According to an aspect of some embodiments there is provided a bone anchor including an elongated core having a tip at a distal end and coupled to a head at a proximal end, and a segmented helical thread defining one or more gaps therein, each gap defining at least a trailing wall, the trailing wall having a cutting surface including at least one cutting edge; the bone cutting surface and the cutting edge configured to cut bone and guide bone fragments radially inwards.

According to some embodiments, the gap defines at least a leading wall being more distal along the helical thread in respect to the trailing wall.

According to some embodiments, a major radius (r2) of a following second wing is greater than a major radius (r1) of a preceding first wing by at least one dimension (X), expressed by the formula $[X=(r2)-(r1)]$ and each subsequent wing expands a major radius of a female thread in bone formed by a preceding wing by at least the dimension (X). According to some embodiments, the bone is cortical bone. According to some embodiments, at least the dimension (X) and a number of turns of the anchor in bone defines the quantity of bone fragments that accumulates in the gap.

According to some embodiments, upon rotation of the anchor, the wings continuously cut bone.

According to some embodiments, the cutting surface area is sized and shaped to, upon rotation of the anchor, push the bone fragments accumulated in the gap along a female thread formed by at least one preceding wing.

According to some embodiments, at least one cutting edge is oriented within 30 degrees of parallel to a thread axis. According to some embodiments, at least one cutting edge is oriented perpendicular to a helix angle of the helical thread.

According to some embodiments, the core has cylindrical geometry. According to some embodiments, the wing is attached to the core along at least one third of the circumference of the shaft.

According to some embodiments, the trailing wall is disposed along a plane that extends radially from a longitudinal axis of the core.

According to some embodiments, the trailing wall is disposed along a plane disposed within 30 degrees from a parallel to a thread axis. According to some embodiments, the trailing wall is concave.

According to some embodiments, at least one of the wings includes a proximally facing surface and a bone facing surface and the proximally facing surface and the bone facing surface are equidistant from each other.

According to some embodiments, a first border of the trailing wall is coupled to a trailing edge of the proximally facing surface to form a cutting. According to some embodiments, a second border of the trailing wall is coupled to a trailing edge of the bone facing surface to form a cutting edge.

According to some embodiments, at least one of the wings includes a circumferential surface parallel to a longitudinal axis of the core and disposed along a major diameter of the wing. According to some embodiments, the circumferential surface and the trailing wall meet at the cutting edge. According to some embodiments, the circumferential surface and the trailing wall meet at an angle between 30 and 90 degrees.

According to some embodiments, circumferential surfaces of a plurality of wings form an imaginary cone.

According to some embodiments, the wing includes a square or rectangular cross section at any point along its length.

According to some embodiments, the cutting surface and cutting edge of the trailing wall are disposed along a radius of the core.

According to some embodiments, the cutting surface and cutting edge of the trailing wall are angled in respect to a radius of the core such that the cutting edge is disposed more distally along the thread that an edge of the cutting surface attached to the core. According to some embodiments, the trailing wall is angled between 0 and 30 degrees in respect to the radius.

According to some embodiments, the head includes a first surface coupled to the core and a second surface facing away from the core. According to some embodiments, a distance between the surface coupled to the core and a most proximal portion of a most proximal wing is between 1 and 3 mm.

According to some embodiments, a major diameter of at least one wing is at least equal to twice the diameter of the core.

According to some embodiments, the anchor includes a distal wingless portion having at least one flute, wherein the distal wingless portion extends between 20 and 40 percent of the core length.

According to some embodiments, the distal wingless portion extends more than 2 mm from the distal tip.

According to an aspect of some embodiments there is provided a drill guide for the bone anchor as recited elsewhere herein including a handle coupled to a body including a bone contacting surface and a bore sized to receive a bone drill, and the bone contacting surface including a wedge extending radially outwards from a rim of the bore and projecting away from the surface.

According to some embodiments, the wedge is shaped to form a recess extending from a rim of a bore drilled in a bone, shaped and sized to receive at least a portion of one of the radially extending wings. According to some embodiments, the drill guide includes a handle; coupled to a body including a bone contacting surface and a bore sized to receive a bone drill and the bone contacting surface including a wedge extending radially from a rim of the bore and projecting away from the surface.

According to an aspect of some embodiments there is provided a bone anchor kit including at least one bone anchor including a head, a core and a segment helical thread defining one or more gaps therein, each gap defining at least a trailing wall the trailing wall having a cutting surface including at least one cutting edge; the bone cutting surface and the cutting edge configured to cut bone and guide bone fragments radially inwards, at least one bone anchor driving tool and at least one bone anchor dedicated drill guide.

According to an aspect of some embodiments of the invention, there is provided a clawed plate having at least one aperture on one end and at least one claw on the opposite end. In some embodiments, the claw is curved in respect to the surface of the plate. In some embodiments, the aperture is sized to accommodate at least a bone anchor. In some embodiments, the aperture comprises a step sized to accommodate art least a shoulder of the bone anchor head.

According to an aspect of some embodiments there is provided a method for implanting a bone anchor in bone including drilling a bore in a cortical layer of the bone, forming a notch in a surface of the bone, placing in the bore a bone anchor including a core and a segment helical thread defining one or more gaps therein, each gap defining at least a trailing wall the trailing wall having a cutting surface including at least one cutting edge such that at least a portion of the cutting edge is positioned inside the slot, rotating and driving the anchor into the bone and cutting bone and guiding bone fragments radially inwards.

According to some embodiments, the notch extends radially from a rim of the bore. According to some embodiments, a diameter of the bore is sized to snuggly accommodate the core.

According to some embodiments, the method further includes placing a fixation device against the bone and placing the bone anchor through an opening in the fixation device into the drilled bore.

According to some embodiments, the method further includes forming a female thread in bone in which a major diameter ($\varnothing_{MD1}$) of the female thread behind a first wing is smaller than a major diameter ($\varnothing_{MD2}$) of said female thread behind a following second wing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A, 2B, 2C, 2D and 2E are side view and cross-section view simplified illustrations of a bone anchor and operation thereof in accordance with some embodiments of the present invention;

FIGS. 7A and 7B are pictorial view simplified illustrations of an exemplary embodiment of a bone anchor;

FIGS. 13A, 13B, 13C, 13D and 13E are pictorial view simplified illustrations of a dedicated drill guide for a bone anchor;

DESCRIPTION OF SPECIFIC EMBODIMENTS OF THE INVENTION

The present invention, in some embodiments thereof, relates to bone anchors and, more particularly, but not exclusively, to self-tapping bone anchors.

Figure 1A:
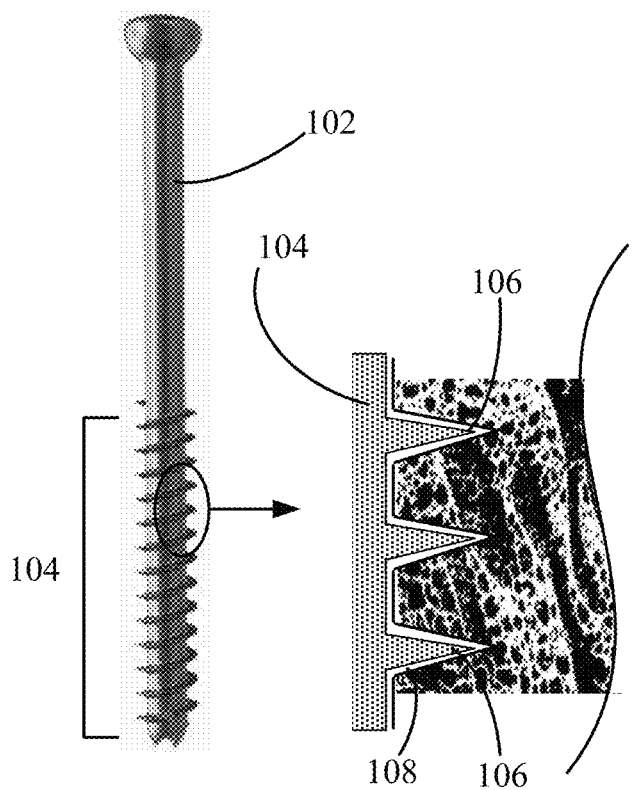
FIG. 1A is a pictorial view illustration of a commonly used cancellous bone screw and a cross-section view illustration of an interaction of a cancellous bone screw thread with cancellous bone.
Figure 1B:
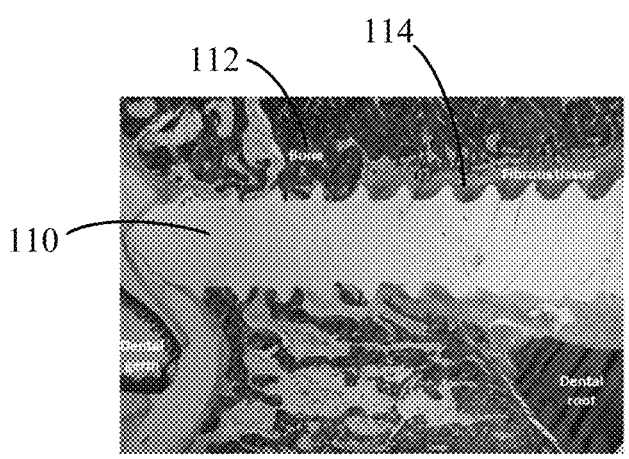
FIG. 1B is an in Vivo Evaluation of immediately loaded stainless steel and titanium orthodontic screws in a growing bone.

For purposes of better understanding some embodiments of the present invention, as illustrated in FIGS. 2A to 20 of the drawings, reference is first made to the construction and operation of a commonly used cancellous bone screw as illustrated in FIGS. 1A and 1B.

Shown in FIG. 1A is a commonly used cancellous bone screw 102 and a cross-section view simplified illustration of a thread 104 of a cancellous bone screw interacting with cancellous bone. Threads 104 of a commonly used cancellous bone screws are typified by having sharp tapered edges 106 along the major diameter of the thread configured to cut into cancellous bone and tap a female thread 108 in which the screw will eventually become embedded. The screw thread 104 cuts into the bone and in some instances may form bone debris that may create binding or wedging during insertion. The binding or wedging during insertion may provide a feel to the surgeon of a solid attachment, but may disappear as pulverized material is resorbed, or further crushed. Some pulverized material may also be lost into crevices and caverns of the cancellous bone. This phenomenon may be seen in FIG. 1B, which is an in Vivo Evaluation of Immediately Loaded Stainless Steel and Titanium Orthodontic Screws in a Growing Bone taken from Kerstin Gritsch, Norbert Laroche, Jeanne-Marie Bonnet, Patrick Exbrayat, Laurent Morgon, Muriel Rabilloud, Brigitte Grosgogeat/Published: Oct. 4, 2013, https://doi(dot)org/10(dot)1371/journal(dot)pone(dot)0076223. Sharp tapered edges 106 commonly compress and crush surrounding bone and force pulverized material in a radially outward direction. Additionally, tapered thread edges often result in the screw placing the bone in a highly stressed condition, with the result that a sharp impact might easily cause the bone to crack.

As a result and as shown in FIG. 1B, several weeks after implantation only a portion of the screw 110 remains in contact with bone 112 while along other portions of the screw thread the bone has been resorbed and replaced by fibrous tissue 114. Fibrous tissue, being weaker than bone, allows for movement of the screw, succumbing to applied pressures and forces leading eventually to loosening and the pulling out of the screw and implant.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As used herein, the term "Proximal" or "Proximally" means close to or in the direction of the anchor head. The term "Distal" or "Distally" means close to or in the direction of the anchor tip and away from the anchor head. As used herein, the term "Leading" refers to a portion of the anchor (e.g., a wall of a gap between a pair of wings) that is more distal along the anchor thread. The term "Trailing" refers to a portion of the anchor (e.g., a wall of a gap between a pair of wings) that is more proximal. In some embodiments, for example, a trailing wall of a gap comprises a leading cutting surface of the wing proximal to the gap.

A "Leading Portion" or "Leading Edge" becomes a corresponding "Trailing Portion" or "Trailing Edge" when the direction of rotation of the anchor is reversed.

The term "Major Radius (r)" as used herein means half of a "Major Diameter (Ø)" of the anchor at the measured level.

An aspect of some embodiments of the invention relates to a bone anchor comprising a core disposed between an anchor head at one end and a tip at an opposite end and wings that form a thread around the core. In some embodiments, the thread comprises a segmented helical thread defining one or more gaps therein. In some embodiments, each gap defines at least a trailing wall having a cutting surface including at least one cutting edge. In some embodiments, the bone cutting surface and cutting edge are configured to cut bone and guide bone fragments radially inwards. In some embodiments, the gap defines at least a leading wall being more distal along the helical thread in respect to the trailing wall.

In some embodiments, the gap trailing wall is operative to push bone fragments accumulated in the gap along a female thread formed by at least one preceding wing. In some embodiments, the gap leading wall is configured to trap and collect bone fragments accumulated in the gap during insertion of the anchor into an implantation site. The bony fragments serve as autografts and promote bone regeneration during the healing process.

In some embodiments, the anchor comprises an elongated core or a stem disposed between and coupled to a head at a proximal end and a tip at a distal end. In some embodiments, the core comprises at least two radially extending wings. In some embodiments, at least one wing comprises a leading portion and a trailing portion. In some embodiments, the leading portion of at least one wing comprises a bone cutting surface having at least one bone cutting edge. In some embodiments, the trailing portion of at least one wing comprises a trailing wall. In some embodiments, the leading bone cutting surface is disposed along a plane parallel to a longitudinal axis of the core and extends radially from the longitudinal axis with an inner border coupled to the core and an outer border at a major diameter of the thread.

In some embodiments, the wings form a segmented helical thread along at least a portion of the core. In some embodiments, the wings are arranged in subsequence so that one wing is followed (but is not in contact with) a subsequent wing along a helical path. In some embodiments, every pair of subsequently arranged wings trap and collect bone fragments in a space disposed in between the wings. In some embodiments, the wings are coupled to and wrap around the core. In some embodiments, the wings wrap around the core along a helical path extending longitudinally along the core from the head of the anchor to the tip.

In some embodiments, the wing comprises at least one proximally facing surface facing the head of the anchor. In some embodiments, the wing comprises at least one distally facing surface facing the tip of the anchor. In some embodiments, the proximally facing and distally facing surfaces are equidistant. In some embodiments, a circumferential surface is coupled at a distal margin to a circumferential edge of the distal surface at a major diameter (Ø) of the wing and at a proximal margin to a circumferential edge of the proximal surface at a major diameter (Ø) of the wing. In some embodiments, the circumferential surface is perpendicular to the proximal and/or distal surfaces. In some embodiments, for any wing 210 a major diameter ($Ø_{MD}$) is at least twice the diameter of the core ($Ø_{md}$). In some embodiments, for any wing a major diameter ($Ø_{MD}$) is between 1.5 and 4 times, 2.5 and 3.5 times, less than twice or more than 4 times the diameter of the core ($Ø_{md}$).

In some embodiments, at least the leading portion bone cutting surface is defined by a radially extending surface. In some embodiments, edges of the bone cutting surface are coupled at an angle to leading edges of the proximal, distal and circumferential surfaces of the wings and the outer surface of the core. In some embodiments, a surface of the bone cutting surface is angled at an angle (α) in respect to a radius (α) of the anchor core at the point of contact of the surface with the anchor core. In some embodiments, angle (α) is between 0 and 50 degrees. In some embodiments, angle (α) is between 0 and 50 degrees 10 and 40 degrees, 20 and 30 degrees more than 50 or less than 0 degrees.

In some embodiments, at least one of coupled edges of the bone cutting surface of the leading portion and the leading edges of the proximal, distal and circumferential surfaces forms a cutting edge. In some embodiments, the bone cutting surface is flat. In some embodiments, the bone cutting surface is at least partially curved. In some embodiments, the bone cutting surface forms concave spoon geometry. In some embodiments, the cutting edge coupling the bone cutting surface and the leading edge of the circumferential surface is positioned further along (down) the thread than the bone cutting surface edge coupled to the core forming an angle between the bone cutting surface and a radius extending through the bone cutting surface edge coupled to the core. In some embodiments, the bone cutting surface angle in respect to a radius extending from the core extending through the bone cutting surface edge coupled to the core is less than 45 degrees, between 0 and 45 degrees, 5 and 30 degrees, 10 and 20 degrees, less than 5 degrees or more than 45 degrees.

In some embodiments, at least the trailing edge comprises a surface defining a radially extending bone cutting surface. In some embodiments, edges of the bone cutting surface are coupled at an angle to trailing edges of the proximal, distal and circumferential surfaces and the outer surface of the core. In some embodiments, the angle is 90 degrees or less. In some embodiments, the angle is between 30 and 90 degrees, 45 and 60 degrees more than 90 or less than 30 degrees. In some embodiments, at least one of coupled edges of the surface of the trailing edge and the trailing edges of the proximal, distal and circumferential surfaces forms a cutting edge. In some embodiments, the bone cutting surface is flat. In some embodiments, the bone cutting surface is at least partially curved. In some embodiments, the bone cutting surface forms concave spoon geometry. In some embodiments, the bone cutting surface edge coupled to the core is positioned further along (down) the thread than the cutting edge coupling the bone cutting surface and the trailing edge of the circumferential surface, forming an angle between the bone cutting surface and a radius extending through the bone cutting surface edge coupled to the core. In some embodiments, the bone cutting surface angle in respect to a radius extending from the core extending through the bone cutting surface edge coupled to the core is less than 45 degrees, between 0 and 45 degrees, 5 and 30 degrees, 10 and 20 degrees, less than 5 degrees or more than 45 degrees.

In some embodiments, the leading portion and trailing portion are defined by a direction of rotation of the anchor. In some embodiments, the trailing portion of one wing and a leading portion of a following wing define a gap between them operative to trap bone fragments carved from the bone during rotation of the anchor by at least one cutting edge of the leading portion of a following wing.

In some embodiments, a major diameter (Ø) of each wing is larger than a major diameter of a subsequently preceding wing. In some embodiments, a single wing extends along any 360 degree full circumference of the core at any wing populated level. In some embodiments, a transverse cross-section of the anchor at a level of any wing transects the core and at least a portion of a single wing. In some embodiments, the heads comprises at least one distally facing surface. In some embodiments, a proximal end of the core is coupled to the distally facing surface of the head. In some embodiments, a distance between the distally facing surface of the head and a most proximal aspect of the most proximal wing equals a thickness of the bone cortex at the point of insertion of the anchor.

An aspect of some embodiments of the invention relates to a drill guide for a bone anchor. In some embodiments, the drill guide comprises a handle and a body having a bore sized and fitted to receive a drill bit. In some embodiments, the bore is centrally located. In some embodiments, the body comprises a distally facing surface comprising at least one wedge. In some embodiments, the wedge projects distally from the distally facing surface of the drill guide body. In some embodiments, the wedge has flat geometry, comprising a sharp distal ridge extending radially outwardly from the bore. In some embodiments, the drill guide body comprises a flat proximally facing surface operative to receive a hammer strike.

An aspect of some embodiments of the invention relates to a combination bone anchor operative to tap a female thread in bone and trap and collect bone fragments during insertion.

In some embodiments, the anchor comprises a core or a stem disposed between and coupled to a head at a proximal end and a tip at a distal end. In some embodiments, the core comprises at least two radially extending wings. In some embodiments, at least a distal portion of the core comprises a cancellous bone driving thread.

In some embodiments, the wings form a segmented helical thread along at least a portion of the core. In some embodiments, the wings are arranged in subsequence so that one wing is followed (but is not in contact with) a subsequent wing along a helical path. In some embodiments, every pair of subsequently arranged wings collect bone fragments in a space disposed in between the wings. In some embodiments, the wings are coupled to and wrap around the core. In some embodiments, the wings wrap around the core along a helical path extending longitudinally along the core from the head of the anchor to the tip. In some embodiments, the most distal wing, closest to the tip has hatchet blade geometry comprising a sharp edge and a trailing wall. In some embodiments, the most distal wing, closest to the tip comprises a regular cancellous bone thread blade and a trailing surface 240.

In some embodiments, all gaps have the same size (volume, length and/or width). In some embodiments, the gaps differ in size. In some embodiments sizes of the gaps (e.g., volume, length and/or width) are in inverse proportion in respect to the major diameter of the wings defining the gap. The greater the major diameter—the smaller the gap is. In some embodiments, the closer the gap is to the anchor head, the smaller the gap is.

An aspect of some embodiments of the invention relates to a bone anchor kit for a bone anchor operative to tap a female thread in bone and collect and preserve bone fragments during insertion.

In some embodiments, the kit comprises at least one bone anchor and at least one bone drill guide. In some embodiments, the kit comprises at least one ratchet operative to drive the anchor into bone. In some embodiments, the anchor comprises a core or a stem disposed between and coupled to a head at a proximal end and a tip at a distal end. In some embodiments, the core comprises at least two radially extending wings. In some embodiments, the wings form a segmented helical thread along at least a portion of the core. In some embodiments, the wings are arranged in subsequence so that one wing is followed (but is not in contact with) a subsequent wing along a helical path. In some embodiments, every pair of subsequently arranged wings collect bone fragments in a space disposed in between the wings.

In some embodiments, the kit comprises a plurality of bone anchors having a variety of sizes. In some embodiments, the kit comprises a plurality of bone anchors having varying distances between a distally facing surface of the head and a most proximal aspect of the most proximal wing that equal various thicknesses of the bone cortex at various points of insertion of the anchor.

In some embodiments, the kit comprises a plurality of bone anchors comprising varying numbers of wings corresponding to the length of the anchor, specific bone and site of insertion into bone.

In some embodiments, the kit comprises at least one combination bone anchor operative to tap a female thread in bone and collect and preserve bone fragments during insertion.

In some embodiments, the anchor comprises a core or a stem disposed between and coupled to a head at a proximal end and a tip at a distal end. In some embodiments, the core comprises at least two radially extending wings. In some embodiments, at least a distal portion of the core comprises a wingless portion.

In some embodiments, the kit comprises at least one bone drill, at least one drill bit, at least one hammer and at least one anchor driver. In some embodiments, the anchor driver comprises a ratchet.

An aspect of some embodiments of the invention relates to a method of securing an implant to bone. In some embodiments, the method comprises driving into bone a bone anchor operative to tap a female thread in bone and collect and preserve bone fragments during insertion. In some embodiments the method comprises placing a drill guide on a surface of bone and forming a notch in the bone. In some embodiments, the method comprises drilling a bore in a surface of a bone, the bore being in continuum with the notch. In some embodiments, the method comprises placing an implant against the bone and placing the bone anchor comprising a stem and at least two radially extending wings coupled to and arrange subsequently to wrap said stem forming a segmented helical thread along at least a portion of said stem through an opening in the implant and into the drilled bore in the bone. In some embodiments, the method comprises rotating the anchor and inserting a distal edge of the most distal wing into the notch formed in the bone and driving the anchor into the bone. In some embodiments, the method comprises collecting bone fragments between at least two subsequent wings during rotation of the anchor.

Bone Anchor Structure

Reference is now made to FIGS. 2A, 2B, 2C, 2D and 2E, which are side view and cross-section view simplified illustrations of a bone anchor and operation thereof in accordance with some embodiments of the present invention. As shown in the exemplary embodiment in FIG. 2A, bone anchor 202 comprises an elongated core or stem 204 disposed between and coupled to a head 206 at a proximal end and a sharp tip 208 at a distal end. In some embodiments, head 206 is similar to the anchor head described in detail in international patent application publication WO2015/186123 which is incorporated herein in its entirety, the description of which will therefore not be repeated.

In some embodiments, head 206 comprises at least one distally facing surface 238. In some embodiments, core 204 comprises at least two radially extending wings 210. In some embodiments, and as shown elsewhere herein, wings 210 form a segmented helical thread 212 along at least a portion of core 204. In some embodiments, wings 210 are arranged in subsequence so that one wing (e.g., FIG. 2D, wing 210-1) is followed (but is not in contact with) a subsequent wing (e.g., FIG. 2D, wing 210-2) along the helical path. In some embodiments, each pair of subsequently arranged wings 210 form a gap 214 in them along the thread in which bone fragments 290 carved out of the bone are trapped and collected as anchor 202 is rotatably driven into the bone and will be explained in greater detail elsewhere herein. The trapped and collected bone fragments serve as bony autografts that promote regeneration of bone during the healing process as explained in greater detail elsewhere herein. In some embodiments, wings 210 are coupled to and wrap around core 204 to form thread 212. In some embodiments, helical path 212 extends longitudinally along core 204 from head 206 of anchor 202 to tip 208.

A potential advantage of the structure of anchor 202 is in that only the cortical bone requires drilling. No drilling is required in cancellous bone since the wings are self-tapping and carve their own female thread path through cancellous bone as they are rotatably driven into the site of implantation.

In some embodiments, at least one wing 210 has ledge geometry. In some embodiments, wing 210 comprises at least one proximally facing surface 216 facing head 206 of the anchor and at least one distally facing surface 218 facing tip 208. In some embodiments, proximally facing surface 216 and distally facing surface 218 are equidistant. In some embodiments, a wing comprises a circumferential surface 220 along a major diameter of wing 210 and parallel to a longitudinal axis of core 204. In some embodiments, a distal edge of circumferential surface 220 is coupled at least at a major diameter (Ø) of wing 210 to a circumferential edge 222 of distal surface 218 and a proximal edge of circumferential surface 220 at least at a major diameter (Ø) of wing 210 to a circumferential edge 224 of proximal surface 216. In some embodiments, circumferential surface 220 is perpendicular to proximal and/or distal surfaces 216/218.

In some embodiments, as shown in the exemplary embodiment depicted in FIG. 2C and explained in greater detail elsewhere herein, any wing 210 comprises a rectangular or square transverse cross-section taken along a radius (e.g. FIG. 2B, r1/r2/r3) anywhere along wing 210.

In some embodiments, at least one wing 210 comprises a leading portion 226 and a trailing portion 228. In some embodiments, at least the leading portion 226 comprises a surface defining a radially extending bone cutting surface 230. In some embodiments and as shown in FIG. 2B, bone cutting surface 230 is flat. In some embodiments and as shown in FIG. 2D, bone cutting surface 230 is curved (concave) in a radial dimension. In some embodiments and as shown in FIG. 2E, bone cutting surface 230 is curved (concave) in both a radial dimension and longitudinal dimension forming a spooned shaped. In some embodiments, meeting edges of bone cutting surface 230 with a leading edge of proximal surface 216, a leading edge of distal surface 218 and/or a leading edge of circumferential surface 220 form one or more bone corresponding cutting edges 232, 234 and 236. In some embodiments, the trailing portion of at least one wing 210 comprises a trailing surface 240.

As explained in greater detail elsewhere herein, as the anchor is turned while being driven into bone, cutting edges 232, 234 and 236 carve bone forming a channel spiraling down along core 204. Carved bone fragments are collected by bone cutting surface 230 and the collected fragments are trapped and built up within gap 214 between a trailing portion of a wing 210 and a leading portion of a following wing 210.

Reference is now made to FIGS. 3A, 3B, 3C and 3D which are a side and bottom view simplified illustrations of a bone anchor.

Figure 3A:
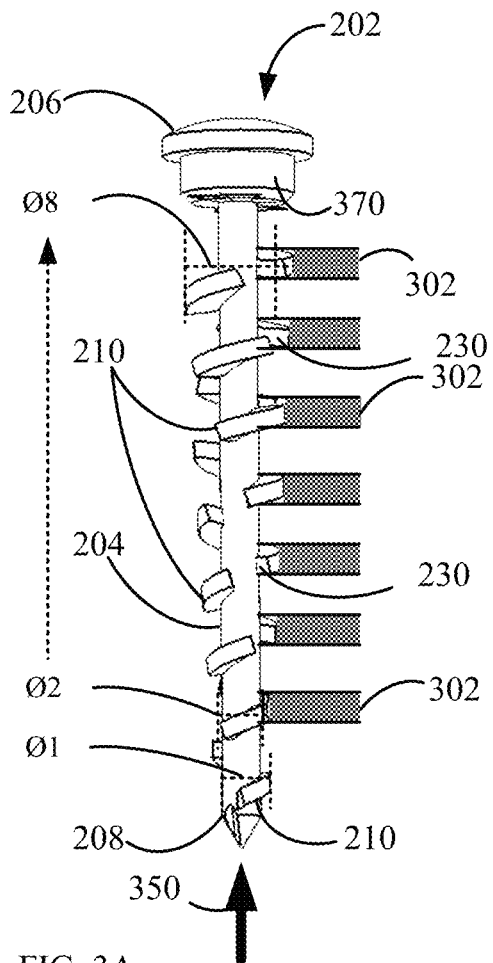
FIGS. 3A, 3B, 3C and 3D are a side and bottom view simplified illustrations of a bone anchor.

As depicted in the exemplary embodiment shown in FIG. 3A, wings 210 of anchor 202 form a segmented thread 212 over at least as portion of core 204. In some embodiments, core 204 is cylindrical, having a constant minor diameter along at least a portion of core 204. Hence and as shown in the example depicted in FIG. 3C, wings 210 comprise a constant minor diameter along at least a portion of core 204 and in some embodiments, an increasing major diameter from tip 208 towards head 206. In some embodiments, for any wing 210 a major diameter ($Ø_{MD}$) of the wing is at least twice the diameter of core 204 ($Ø_{MD}$). In some embodiments, for any wing 210 a major diameter ($Ø_{MD}$) is between 2 and 4 times, 2.5 and 3.5 times, less than twice or more than 4 times the diameter of core 204 ($Ø_{md}$).

As used herein, the term "Major Diameter" is the larger of two extreme diameters delimiting the height of a thread profile, as a cross-sectional view is taken in a plane containing the axis of the threads and the term "Minor Diameter" is the lower extreme diameter of the thread.

As shown in the example in FIG. 3A, a major diameter (Ø8) of wing 210 closest to head 206 is much greater than a major diameter (Ø1) of wing 210 closest to tip 208. In some embodiments, major diameter (Ø8) is between 2 and 8 times major diameter (Ø1), between 3 and 6 times major diameter (Ø1), between 4 and 5 times major diameter (Ø1), less than twice major diameter (Ø1) or more than 8 times major diameter (Ø1).

Figure 3B:
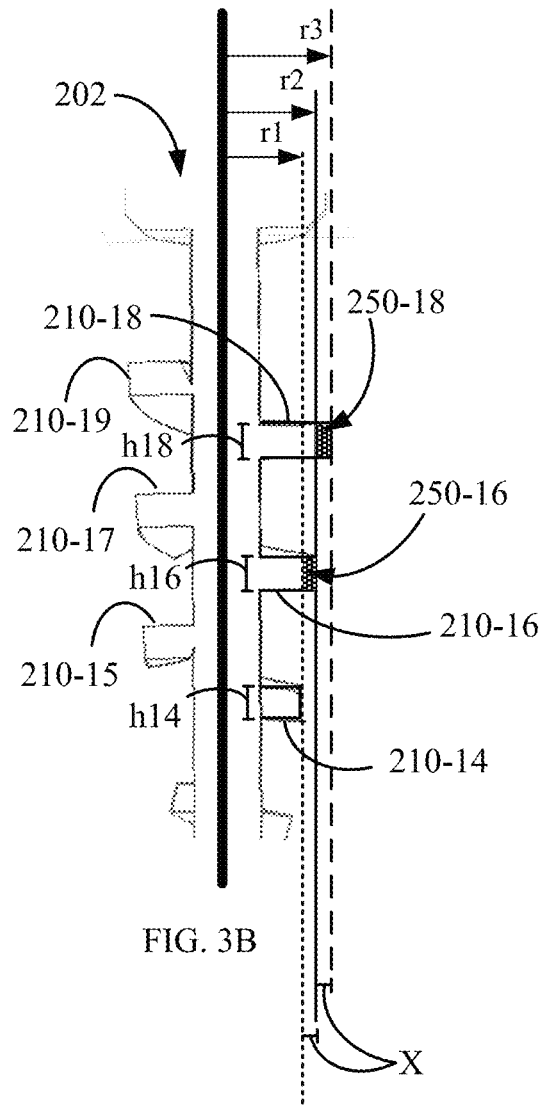
Figure 3C:
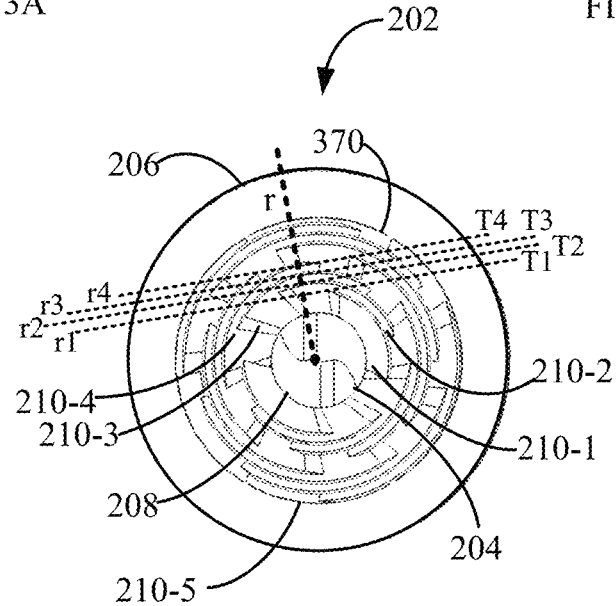

The increase in the major diameter (Ø) of wings 210 the closer they are to head 206 is also shown in FIG. 3B, which is a longitudinal sectional simplified illustration of a portion of the exemplary embodiment shown in FIGS. 2A-E, taken along axis A-A. As shown in the example depicted in FIG. 3B, the major diameter (Ø) of wing 210-18 (i.e., 2*r3) is greater than the major diameter (Ø) of wing 210-16 (i.e., 2*r2), which in turn is greater than the major diameter (Ø) of wing 210-14 (i.e., 2*r1). The effective cutting portion 250-18 of the surface of a leading bone cutting surface 230 for wing 210-18 would therefore be the thickness/height (h18) of the wing multiplied by the difference (r3−r2) between the radius (i.e., half major diameter) of 210-18 and the radius of wing 210-16 preceding wing 210-18 along the thread. Hence, in some embodiments, each wing 210 cuts a fragment of bone (e.g., cortical bone) having at least one dimension (X) equal, for example, to (r2) less (r1), i.e., X=(r2)−(r1). Accordingly, the effective cutting portion 250-16 of the surface of a leading bone cutting surface 230 for wing 210-16 would therefore be the thickness/height (h16) of the wing multiplied by the difference (r2−r1) between the radius (i.e., half major diameter) of 210-16 and the radius of wing 210-14 preceding wing 210-16 along the thread. In FIG. 3B, only wings 210-15/210-17 and 210-19 have been ignored for the purpose of simplifying the explanation however it should be noted that as explained elsewhere herein, the major diameter (2*r) of each wing 210 increases in accordance with the progression of wing reference numerals from 210-14 to 210-19.

In some embodiments, at least the dimension (X) and a number of turns of the anchor in the bone define the quantity of bone fragments that accumulates in the gap. Hence, once the anchor is fully inserted in bone, the number of the fragments in gaps 214 will depend on the axial location of the gap. The more distal the gap—the greater will be the quantity of bone fragments in gap 214. Hence, in more distal gaps 214 the quantity of accumulated bone may exceed the volume of gap 214 and bring about radially inward compression of the bone fragments.

In some embodiments, the thicknesses of the wings are the same. In some embodiments, the thicknesses of the wings vary.

The arrangement of the wings in a growing major diameter order is set to provide each wing 210 with a bite off a fragment of cortical bone 302 before entering cancellous bone. The fragment of cortical bone together with cancellous bone fragments collected while anchor 202 is driven into the bone serve as boney autografts that promote bone tissue regeneration during the healing process. In FIG. 3A, several cortical layers 302 are drawn (each next to each wing 210) for explanatory reasons only, to demonstrate the progressively growing size of bites taken by wings 210 from cortical bone layer 302 as each wing is driven through cortical layer 302 and as the major diameter of the wing increases in size the closer the wing 210 is to head 206. This is also shown in FIG. 3B, which is a bottom view simplified illustration of bone anchor 202 viewed in the direction indicated by arrow 350 of FIG. 3A. As shown in FIG. 3B, four tangential lines T1, T2, T3 and T4 are drawn tangent to a major diameter of four subsequent wings 210: 210-1, 210-2, 210-3 and 210-4 wherein 210-1 is the most distal wing and 210-4 is the most proximal wing. As illustrated in FIG. 3B, the major diameter (Ø1) of wing 210-1 being twice radius (r1) at point of tangent T1 is much smaller than the major diameter (Ø4) of wing 210-4 being twice radius (r4) at point of tangent T4.

Wing 210-5 being closest to a head 206 comprises the same diameter as a shoulder 370 of head 206 so that to prepare a bore in the cortical bone that will tightly and precisely accommodate shoulder 370 and help prevent "rocking" of anchor 202 after insertion as described in greater detail in the related International Application Publication WO2015/186123 incorporated by reference herein in its entirety.

Figure 4A:
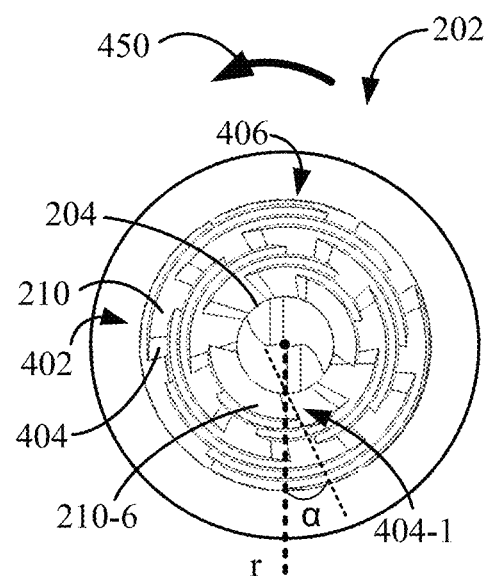
FIGS. 4A, 4B, 4C and 4D are bottom view simplified illustrations of a bone anchor.
Figure 3D:
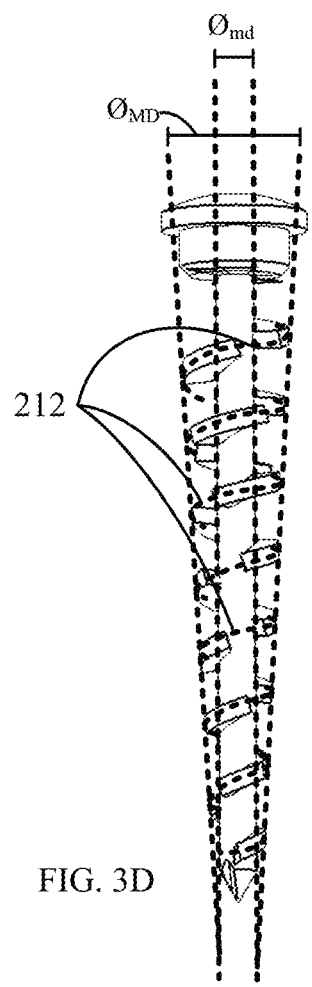

Reference is now made to FIGS. 4A, 4B, 4C and 4D which are bottom view simplified illustrations of anchor 202 viewed from a direction indicated by arrow 350 of FIG. 3A. In FIG. 4A, the direction of rotation of anchor s defined by a curved arrow 450. The direction of rotation defines for each wing 210 a leading portion 402 comprising a cutting surface 404 and a trailing portion 406. As described elsewhere herein, the leading and trailing portions 402/406 respectively are defined by the direction of rotation indicated by arrow 450. However, reversal of the direction of rotation redefines leading portion 402 as a trailing portion and trailing portion 406 as a leading portion having a cutting edge 408.

Figure 4B:
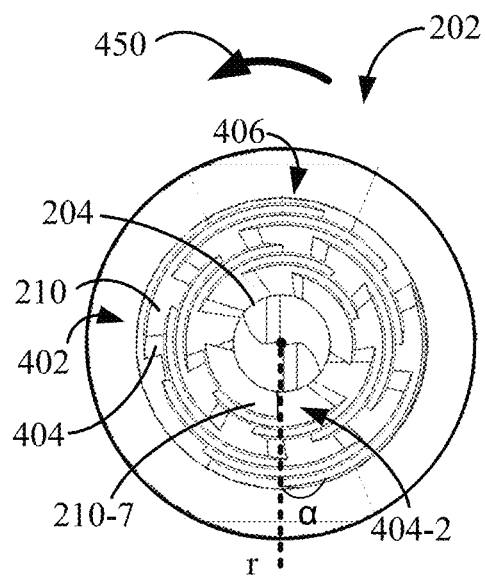
Figure 4C:
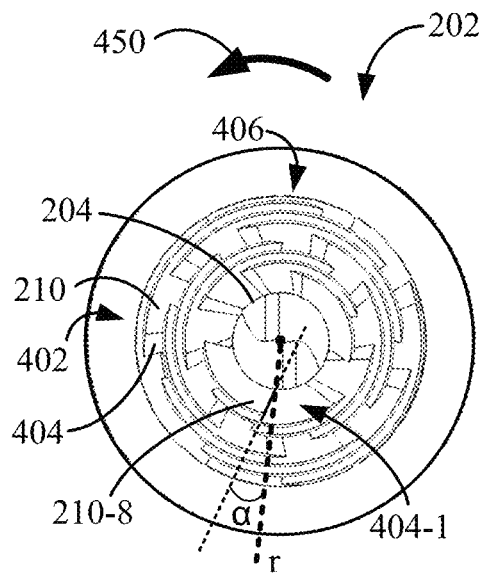

In some embodiments and as shown in FIG. 4A, the surface of a bone cutting surface, for example bone cutting surface 404-1 of wing 210-6, is at an angle (a) in reference to a radius (r) of anchor 202 at the point of contact of the surface of surface 404 with core 204 and with respect to the direction of rotation indicated by arrow 450. In this configuration, the edge of surface 404 at the major diameter of wing 210-6 is more advanced in reference to the direction of rotation of anchor 202 than the edge of the surface of wall 404-1 coupled to core 204. In some embodiments, angle (α) is between 0 and 50 degrees. In some embodiments, angle (α) is between 0 and 50 degrees 10 and 40 degrees, 20 and 30 degrees more than 50 or less than 0 degrees. As shown in FIG. 4B, the surface of a bone cutting surface, for example a bone cutting surface 404-2 of wing 210-7, is disposed along a radius (r) of anchor 202, at an angle (α) of 0 (zero) degrees in reference to a radius (r) of anchor 202 at the point of contact of the surface of wall 404-2 with core 204. As shown in FIG. 4B, the surface of a bone cutting surface, for example a bone cutting surface 404-2 of wing 210-7, is at a negative angle (α) in reference to a radius (r) of anchor 202 at the point of contact of the surface of surface 404-2 with core 204 and with respect to the direction of rotation indicated by arrow 450.

A potential advantage of an angled bone cutting surface 404 is in that the angle provides surface 404 with a greater cutting surface area than a surface aligned with the anchor radius.

Another potential advantage of an angled bone cutting surface 404 is in that the angle enables surface 404 to push bone fragments along female thread 412 while guiding the bone fragments radially inwards urging the fragments centrally, closer to core 204.

As explained elsewhere herein, a potential advantage of a concavity of the surface of leading bone cutting surface 230 is in that it enables surface 230 to cup bone fragments and better keep the fragments from being pulverized ands or urged radially outward into crevices and caverns of the cancellous bone.

One or more leading edges of circumferential surface 220 form one or more bone corresponding cutting edges 232, 234 and 236. In some embodiments, the trailing portion of at least one wing 210 comprises a trailing surface 240.

As explained in greater detail elsewhere herein, as the anchor is turned while being driven into bone, cutting edges 232, 234 and 236 carve bone forming a channel spiraling down along core 204. Carved bone fragments are collected by bone cutting surface 230 and the collected fragments are trapped and built up within gap 214 between a trailing portion of a wing 210 and a leading portion of a following wing 210.

Figure 4D:
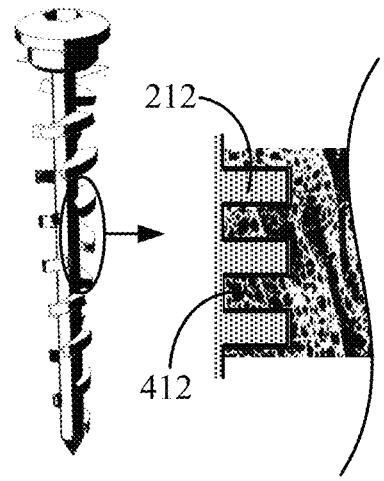

The exemplary embodiment depicted in FIG. 4D demonstrates an example of a female thread 412 carved out of the bone by anchor 202 wings 210. A circumferential surface 410 of female thread 412, mirroring circumferential surface 220 along great diameter ($\emptyset_{MD}$) of anchor 202, is blunt.

A potential advantage of female thread having a blunt circumferential surface is in that such a surface minimizes compression and crushing of surrounding bone and the associated driving of pulverized material in a radially outward direction as seen in commonly used cortical bone screws and explained elsewhere herein.

Bone Anchor Wings Operation

Reference is now made to FIGS. 5A, 5B, 5C, 5D and 5E which are pictorial simplified illustrations of the modus operandi of bone anchor 202. Wings 210 of anchor 202, when driven into bone, tap or cut bone fragments from the bone and collect, preserve and drive the bone fragments along with anchor 202.

A potential advantage of collecting and preserving the bone fragments is in that the fragments become centers for bone tissue regeneration in contact with bone anchor 202 stem 204 and wings 210. For all practical purposes, anchor 202 performs autogenous bone tissue transplantation as it is implanted in to the bone tissue.

Figures 5A, 5B, 5C, 5D:
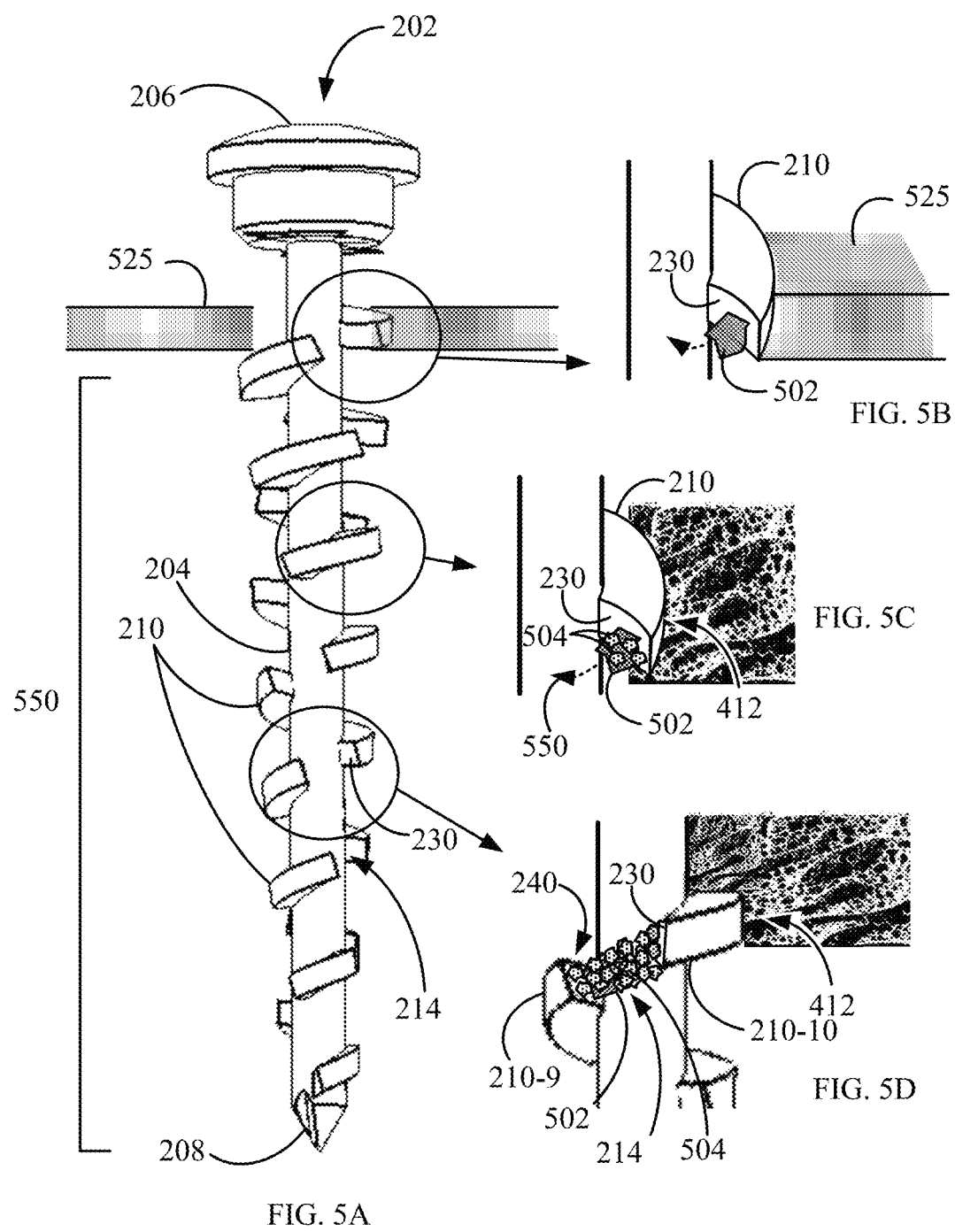
FIGS. 5A, 5B, 5C, 5D and 5E are pictorial simplified illustrations of the modus operandi of a bone anchor.

As shown in FIG. 5A, as anchor 202 is driven into bone tissue, wings 210 first encounter a layer 525 of cortical bone. At the cortical bone level, each wing 210 breaks off a fragment 502 of cortical bone as illustrated in FIG. 5B. As anchor 202 is rotated and wings 210 are advanced along a previously formed female thread 412, wings 210 are driven into cancellous bone. At the cancellous bone level and as shown in the exemplary embodiment depicted in FIG. 5C, each wing 210 taps a new female thread 412 in the cancellous bone having a major diameter ($\emptyset_{MD}$) than thread 412 tapped by the preceding wing 210. Cancellous bone fragments 504 broken off the previously tapped boney thread, together with cortical bone fragments 502 are pushed along female thread 412 by cutting surface 404, as indicated by a broken arrow 550 and accumulated, as shown in FIG. 5D, in gap 214 between trailing surface 240 of wing 210-9 and leading bone cutting surface 230 of wing 210-10.

Figure 5E:
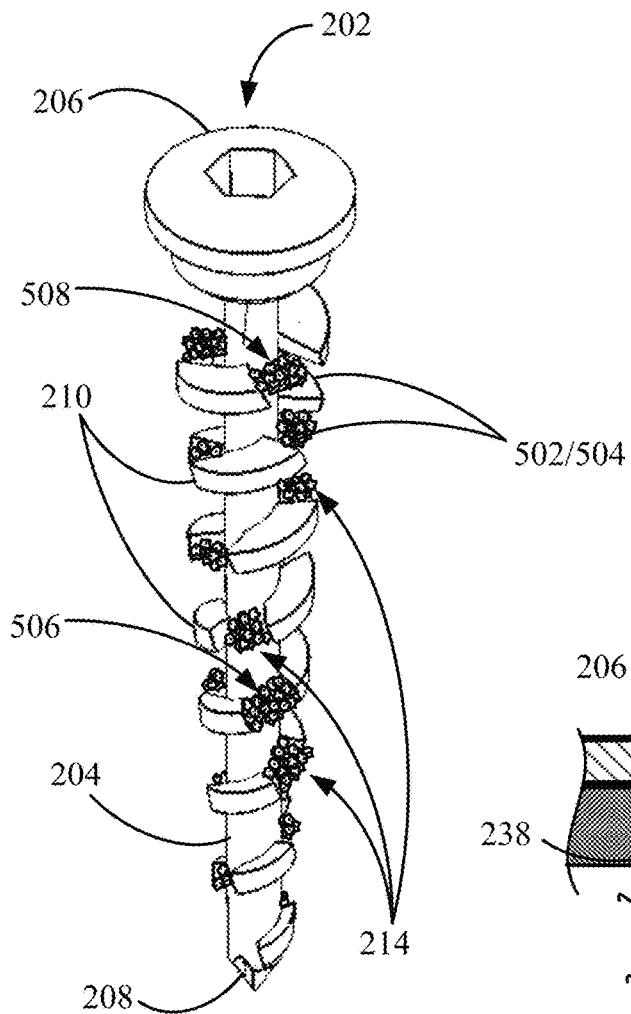

FIG. 5E illustrates anchor 220 in a final state of implantation in which all gaps 214 are filled with cortical and cancellous bone fragments 402/404 respectively forming a continuous fill of female bone thread 412 with alternating anchor 202 wings 210 and bone fragments 502 and 504. As described elsewhere herein, bone fragments 502 and 504 trapped in gap 214 promote bone regeneration locking wings 210 in regenerated bone.

As depicted in FIG. 5E, the farther the gap is from anchor head 206, e.g., gap 506, the fuller it becomes with bone fragments and debris. This is because cutting surfaces of leading walls of consecutive wings defining gap 506 continuously cut bone as anchor 202 is rotated, by at least a dimension (X) as explained in greater detail elsewhere herein and have turned more times than those defining gaps e.g., gap 508 closer to head 206, and have therefore traveled a greater distance along the female thread and accumulated more bone fragments and debris. In some embodiments, all gaps in a bone anchor comprise the same size. In some embodiments, a bone anchor comprises gaps of varying sizes e.g., volume, length and/or width. For example, in some embodiments, gaps between consecutive wings do not necessary fill completely with fragments of bone tissue to allow growth of the accumulated bone tissue just as does an implanted bone graft. Alternatively, and optionally, gaps between consecutive wings located distally may extend along a greater length of the anchor thread, e.g., 1.25, 1.5, 2, 2.25, 2.5, 3 times longer, less than 1.25 times longer, more than 3 times longer or any value in between, than gaps between consecutive wings located more proximally. This is since gaps that have "traveled" a longer distance (i.e., more anchor rotations) accumulate more debris than gaps that have "traveled" a shorter distance (i.e., less anchor rotations). The more distally located is the gap, the more distance (i.e., rotations) it "travels".

However, in some embodiments, sizes of the gaps (e.g., volume, length and/or width) are in inverse proportion in respect to the major diameter of the wings defining the gap, e.g., the greater the major diameters of the consecutive wings defining the gap the smaller the gap size. For example, in short screws, the gap between consecutive wings especially close to the anchor head 206 such as gap 508 may be too large for the expected amount of bone tissue fragments expected to accumulate in the gap. Hence, a distance between a trailing surface of a first wing and a leading surface of a following wing defining a length of the gap in between may be shorter the closer the gap is to anchor head 206. In such embodiments, gap 506 may be larger in volume, length and/or width than the following gap and so on up to gap 508 which is the smallest.

Figure 6:
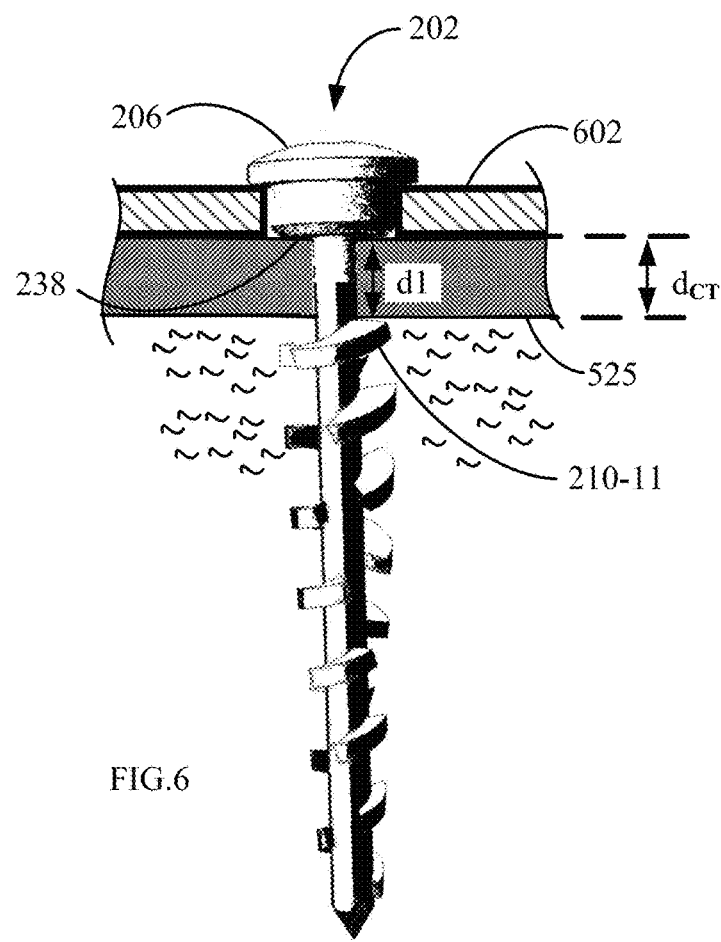
FIG. 6 is a pictorial view simplified illustration of an implanted bone anchor.

Reference is now made to FIG. 6, which is a pictorial view simplified illustration of an implanted anchor 202. As shown in the exemplary embodiment depicted in FIG. 6, anchor 202 is shown to be fixing a support device 602 (e.g., a bone plate) to bone. In some embodiments, the most proximal wing 210-11 is located at a distance (d1) from head 206 distally facing surface 238. In some embodiments, distance (d1) corresponds to a thickness ($d_{CT}$) of a cortical bone layer 525 at the site of anchor 202 implantation. In some embodiments, (d1) is between 1 and 10 mm, 2 and 8 mm, 3 and 6 mm, 4 and 5 mm, less than 2 mm or more than 10 mm.

A potential advantage in a distance (d1) between the most proximal wing 210-11 and distally facing surface 238 is in that cortical bone regeneration inwards, into the gap between the most proximal wing 210-11 and distally facing surface 238 and encloses on core 204 providing added stability to anchor 202 by reducing "rocking" movement of the anchor as well as increasing resistance to pullout forces acting on anchor 202.

FIGS. 7A and 7B are pictorial view simplified illustrations depicting an exemplary embodiment of an anchor 702. Anchor 702 comprises a wingless distal portion 704. In some embodiments, wingless distal portion 704 includes a cutting flute 708. In some embodiments, flute 708 is parallel to a longitudinal axis of core 204. As described elsewhere herein, only the cortical bone layer 525 requires drilling that provides a directional guiding bore for insertion of wingless distal portion 704 of anchor 702. Hence, wingless distal portion 704 extends proximally from tip 208 for a distance (d2) that corresponds to a thickness of the cortical bone layer 525 at the site of implantation. In some embodiments, (d2) is equal to, greater or smaller than the thickness ($d_{CT}$) of cortical bone layer 525. In some embodiments, (d2) is between 1 and 10 mm, 2 and 8 mm, 3 and 6 mm, 4 and 5 mm, less than 2 mm or more than 10 mm.

A potential advantage in the structure of anchor 702 is in that penetration of wingless distal portion 704 of anchor 202 core 204 into cancellous bone 706 displaces and compresses cancellous bone 706-1 radially outward along stem 204 as indicated by arrows designated reference numeral 750. Further rotational insertion of anchor 702 into cancellous bone 706 drives wings 210 to carve the already compressed cancellous bone 706 and collect a greater volume of fragments than in a configuration in which cancellous bone 706 not been previously compressed.

Figure 8:
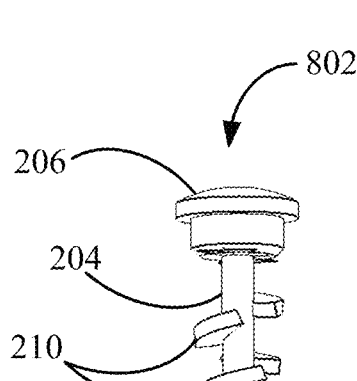
FIG. 8 is a pictorial view simplified illustration of an exemplary embodiment of a bone anchor.
Figure 9:
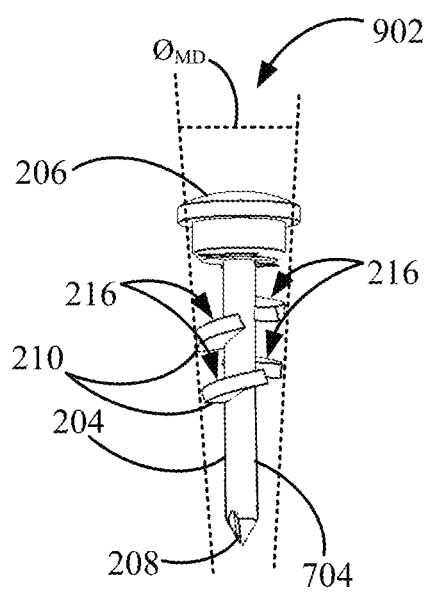
FIG. 9 is a pictorial view simplified illustration of an exemplary embodiment of a bone anchor.
Figure 10:
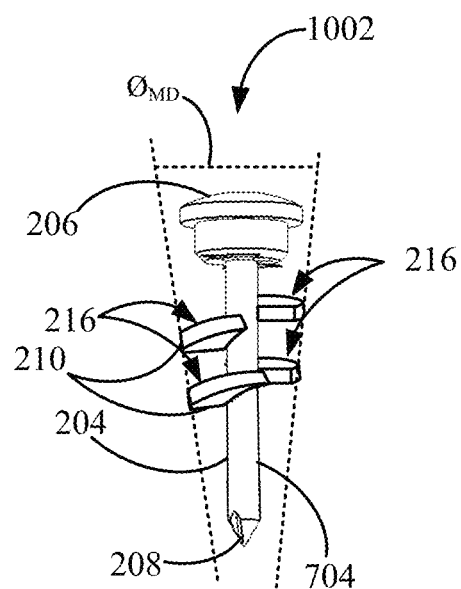
FIG. 10 is a pictorial view simplified illustration of an exemplary embodiment of a bone anchor.

Reference is now made to FIGS. 8, 9 and 10 which are pictorial view simplified illustrations of exemplary embodiments of a bone anchor. As shown in FIGS. 8-10, a bone anchor 802/902/1002 has two or more pairs of wings 210 and varying lengths of core 204.

In some orthopedic situations and in some embodiments, two pairs (four wings) comprise a combined surface area (e.g., combined surface area of proximally facing surfaces 216 of wings 210) to prevent "rocking" motion and pullout of anchor 802/902 after implantation. For example, anchor 902, having a short core 204 may be suitable for implantation in areas having limited bone depth such as in infant bones in pediatric orthopedics or dental surgical procedures. A length of an anchor such as the example illustrated in FIG. 9 for dental procedures may be between 3 and 20 mm, 5 and 15 mm, 8 and 12 mm, less than 3 mm or more than 12 mm.

In some embodiments, stress calculations may show an increased requirement for wing surface area with limited depth of bone. FIG. 10 depicts an exemplary embodiment in which, with respect to bone anchor 902 of FIG. 9, wings 1010 have a greater major diameter than wings 210 of FIG. 9 and therefore an increased surface area of, for example, combined surface area of proximally facing surfaces 1016 of wings 1010 that prevent "rocking" motion and pullout of anchor 1010 after implantation despite the limited available bone depth.

Figure 11:
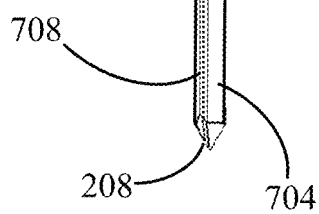
FIG. 11 is a pictorial view simplified illustration of an exemplary embodiment of a bone anchor.

FIG. 11, which is a side view simplified illustration of an exemplary embodiment of a bone anchor, depicts an anchor 1102 similar to anchors described elsewhere herein comprising one or more notches or perforations 1150 in core 1104. Notches or perforations 1104 promote growth of bone tissue into the pores or notches increasing stability and fixation of anchor 1102 in the bone. In some embodiments, bone anchor 202, 702, 802, 902, 1002, 1102, 1202, 1222, 1402 and 1452 are coated with an anti-loosening coating such as Trabecular Structures™ (Manufactured by Arcam AB, Headquarters Krokslätts Fabriker 27ASE-431 37 Mölndal, Sweden).

FIGS. 12A, 12B, 12C and 12D, which are cross-section view simplified illustrations of bone anchor 202 wings 210 illustrate examples of proximally facing and/or distally facing surfaces 216/218 respectively of wings 210 comprising greater surface areas than square or rectangle cross-sections of wings 210. The cross-sections are taken along a radius extending from core 204 radially outwards as shown and discussed elsewhere herein.

Figure 12A:
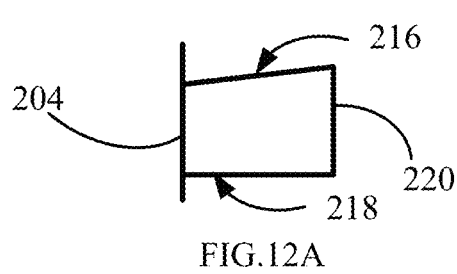
FIGS. 12A, 12B, 12C and 12D are cross-section view simplified illustrations of bone anchor wings in accordance with some embodiments of the current invention.

In the example shown in FIG. 12A, a proximally facing surface 216 is angled and slants radially inwards (from circumferential surface 220 towards core 204). Angled surface 216 does not only provide greater resistance to pullout but also helps maintain bone fragments close to core 204 and preventing such fragments from moving radially outwards.

Figure 12B:
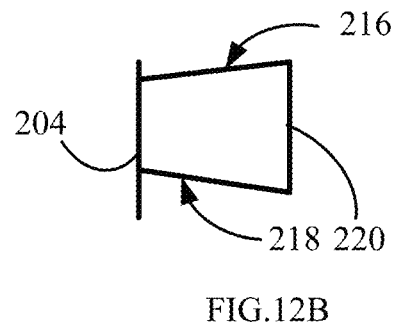

FIG. 12B shows an exemplary embodiment similar to that depicted in FIG. 12A in which distally facing surface 218 is angled and slants radially inwards (from circumferential surface 220 towards core 204) similarly to proximally facing surface 216. The increased surface area of distally facing surface 218 provides greater resistance to further advancement of anchor 1002 succumbing to longitudinal forces resulting from, for example, chewing.

Figure 12C:
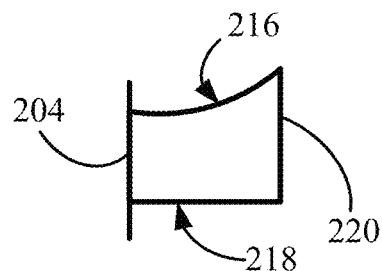
Figure 12D:
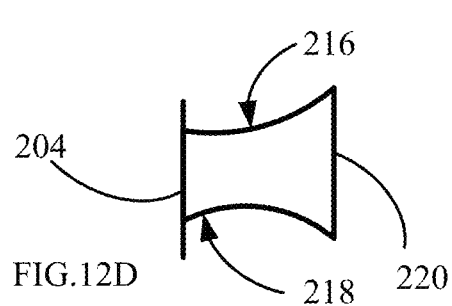
Figure 13A:
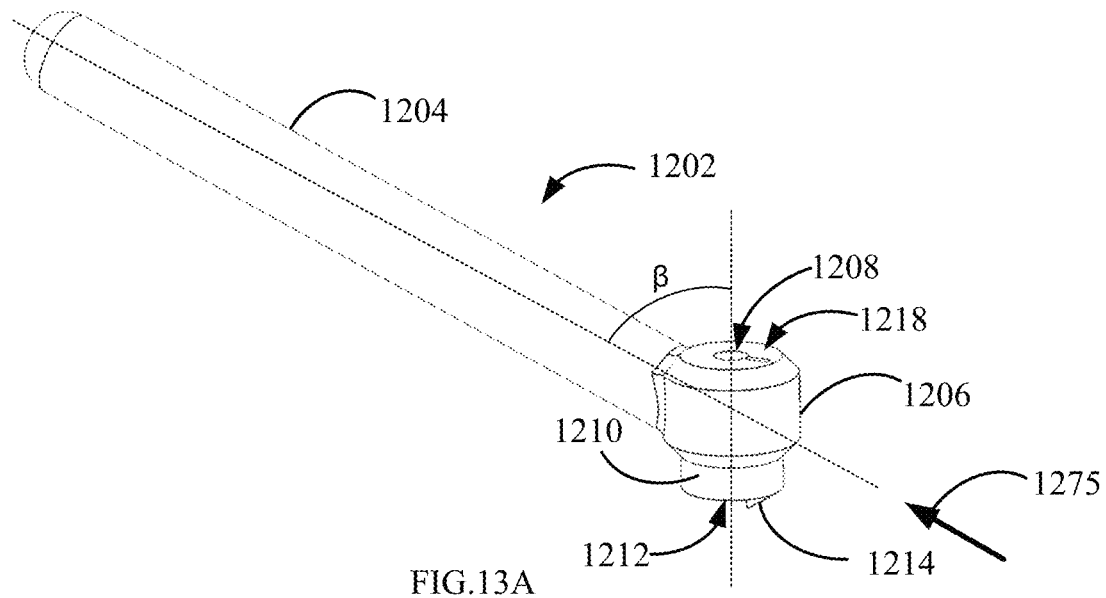

FIGS. 12C and 12D comprise convex proximally facing and/or distally facing surfaces 216/218 respectively of wings 210. Similar to the exemplary embodiments depicted in FIGS. 12A and 12B, concave surfaces 216 do not only provide greater resistance to pullout but also help maintain bone fragments close to core 204 and prevent such fragments from moving radially outwards. Similarly, an increased surface area of distally facing surfaces 218 provides greater resistance to further advancement of anchor 1002 succumbing to longitudinal forces resulting from, for example, chewing.

Dedicated Drill Guide

Reference is now made to FIGS. 13A, 13B, 13C, 13D and 13E, which are pictorial view and partially sectional view simplified illustrations of a dedicated drill guide 1202 for a bone anchor as described elsewhere herein. In some embodiments, drill guide 1202 comprises at least one handle 1204 and a body 1206 having a bore 1208 sized and fitted to receive a drill bit (not shown). In some embodiments, bore 1208 is centrally located. Optionally, a longitudinal axis of handle 1204 is angled at an angle (β) in respect to the longitudinal axis of bore 1208 so that the hand of the surgeon does not contact tissue when placing body 1206 against bone. Optionally, angle (β) is between 10 and 45 degrees, 15 and 40 degrees, 20 and 35 degrees, less than 10 degrees or more than 45 degrees.

In some embodiments, body 1206 comprises a protrusion 1210 on a bone facing aspect of body 1206, sized and fitted to be received by a bone anchor head 206 receiving opening in an implant 1230. For example, such an implant can be a bone plate or a cementless joint resurfacing system as described in International Patent Application No. PCT/IL2016/050818 to the same inventor and is hereby incorporated herein in its entirety.

In some embodiments, protrusion 1210 is cylindrical. In some embodiments and as shown in FIG. 13D, body 1206 protrusion 1210 is sized and fitted to be received by a bone anchor head 206 receiving opening 1228 in an implant 1230 surface, e.g., a bone plate. In some embodiments, the diameter of protrusion 1210 is sized to snugly fit inside opening 1228 in an implant 1230. This is to ensure that drill guide bore 1208 is centered correctly in respect to implant 1230. In some embodiments, body 1206 comprises a bone facing surface 1212 and a surface 1212 facing away from bone. In some embodiments, bone facing surface 1212 is flat. In some embodiments, bone facing surface 1212 is curved and/or angled.

In some embodiments, body 1206 bone facing surface 1212 comprises at least one sharp wedge 1214. In some embodiments, wedge 1214 projects distally from bone facing surface 1212 of drill guide body 1206. In the exemplary embodiment depicted in FIGS. 13A-13D wedge 1214 comprises flat elongated blade-like geometry, having a sharp ridge 1216 and extending radially outwardly from bore 1208. In some embodiments, drill guide body 1206 comprises a flat proximally facing surface 1218 operative to receive a hammer strike.

In some embodiments, and as shown in FIG. 13E walls of drill guide 1222 body 1226 are curved so that drill guide 1222 specifically fits between teeth 1250 to contact bone 1252.

In FIGS. 14A-14D, 15A-15D and 16, bone implant 1230 has been removed to simplify the explanation.

Figure 14A:
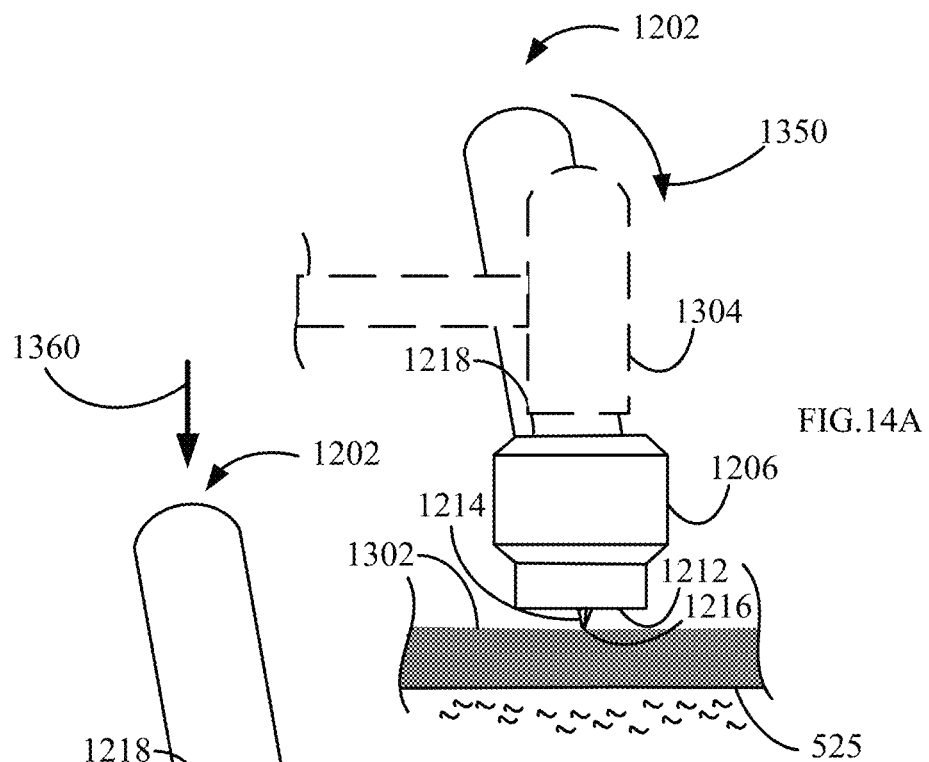
FIGS. 14A, 14B, 14C and 14D are pictorial view simplified illustrations of employment of a dedicated drill guide for a bone anchor.
Figure 14B:
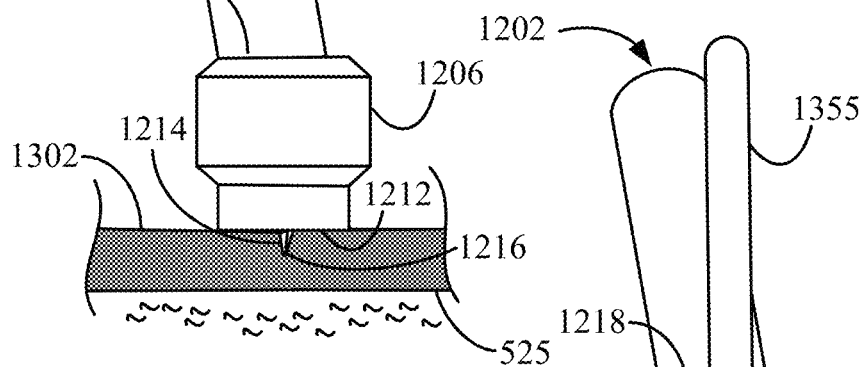
Figure 14C:
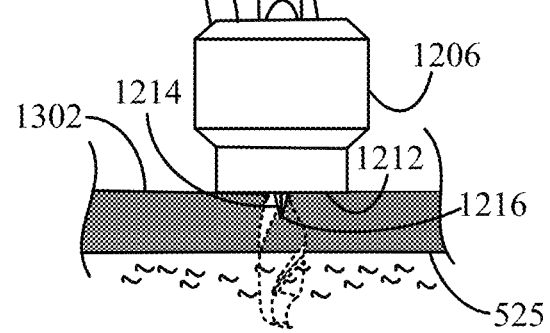

Referring now to FIGS. 14A, 14B and 14C, which are pictorial view simplified illustrations of employment of drill guide 1202 in drilling a bore in cortex of a bone in preparation for implantation of a bone anchor, viewed from a direction indicated in FIG. 12A by an arrow 1275.

As shown in FIG. 14A, drill guide 1202 is placed on surface of a bone at a site of anchor implantation such that sharp ridge 1216 of wedge 1214 engages surface 1302 of bone cortex 525. Once in place, a hammer 1304 is used to tap proximal surface 1218 of body 1206 in a direction indicated by an arrow 1350 and drive wedge 1214 at least partially into cortical bone layer 525. As shown in the exemplary embodiment depicted in FIG. 14B, wedge 1214 is driven into cortical bone 525 until at least a portion of bone facing surface 1212 engages surface 1302 of cortical bone 525. Once body 1206 of drill guide 1202 is firmly placed against surface 1302 of cortical bone 525, a drill bit 1355 may be inserted into bore 1208 and a bore 1306 drilled through cortical layer 525 as shown in FIG. 14C. As explained elsewhere herein, no drilling is necessary in cancellous bone.

At this stage, drill 1306 and drill guide 1202 are removed. In some embodiments, drill guide 1202 may be made of disposable materials and may be disposed of at this stage.

Figure 14D:
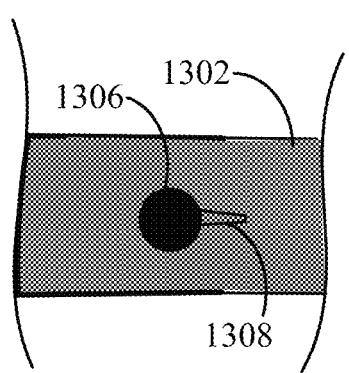

FIG. 14D, shows surface 1302 of cortical bone 525 viewed from a direction indicated in FIG. 14B by an arrow 1360 once drill guide 1202 and drill bit 1355 have been removed. Bore 1306 extends the full thickness of cortical bone layer 525 and a notch 1308 extending superficially radially outward from bore 1306. In the example depicted in FIG. 14D, notch 1308 has slot geometry with a depth equivalent to the height (h) of wedge 1214 from bone facing surface 1212. In some embodiments, height (h) may be between 0.1 and 1 mm, 0.2 and 0.8 mm, 04 and 0.6 mm, less than 0.1 or more than 1 mm.

Reference is now made to FIGS. 15A, 15B, 15C and 15D, which are cross-section view simplified illustrations of positioning of an anchor 202 in a bore 1306 drilled through cortical bone layer 525 with or without a notch 1308 and exemplary embodiments of anchor 202 distal ends and tips. As shown in the exemplary embodiment depicted in FIG. 15A, cortical bone layer 525 comprises a drilled bore 1306 with no notch in surface 1302. Tip 208 of anchor 202 is placed inside bore 1306, however, anchor 202 is positioned at an angle in respect to surface 1302 of cortical bone layer 525. The angle may be created by positioning distally facing surface 218 of wing 210-12 against surface 1302 of the bone providing a surgeon with a false feeling of a close fit of anchor 202 in bore 1306.

Figure 15A:
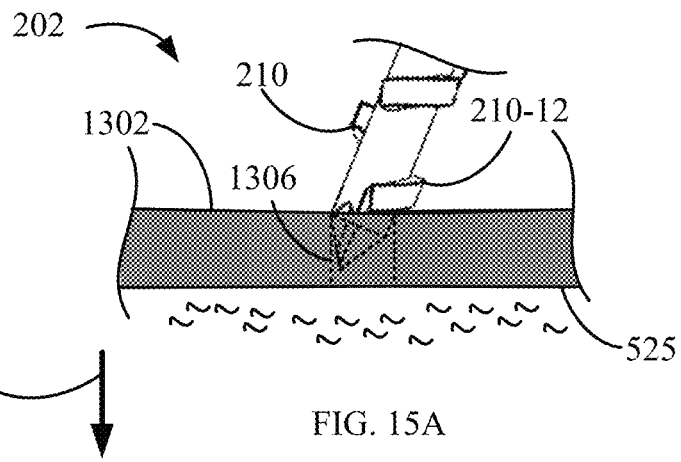
FIGS. 15A, 15B, 15C and 15D are cross-section view simplified illustrations of positioning of a bone anchor in a bore drilled through a cortical bone layer.
Figure 15B:
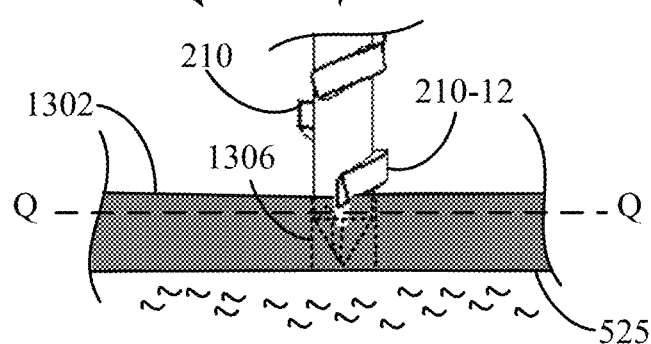

In the exemplary embodiment shown in FIG. 15B, cortical bone layer 525 comprises both a drilled bore 1306 and a notch 1308 in surface 1302 of the bone. In this configuration, tip 208 of anchor 202 is placed inside bore 1306 and at least a portion of leading portion 226 of wing 210-12 is received within notch 1308 and allows the correct positioning of anchor 202 in respect to surface 1302.

A potential advantage in notching the surface 1302 of cortical bone layer 525 is in that it allows correct positioning of anchor 202 in respect to surface 525.

Figure 16:
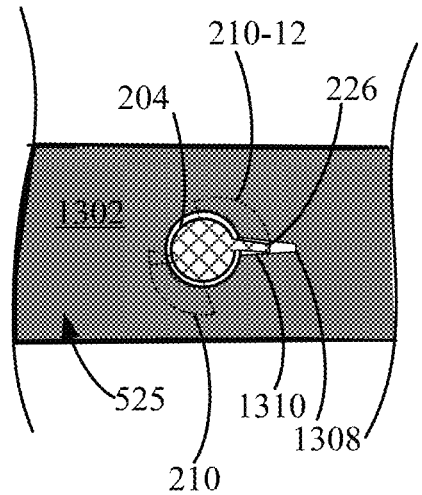
FIG. 16 is a cross-section view simplified illustration of a drilled bore and a notch made in bone.

A potential advantage in notching the surface 1302 of cortical bone layer 525 is in that notch 1308 provides an initial grip of a portion of cortical bone for bone cutting surface 230 when anchor 202 is rotated. This is shown in FIG. 16, which is a cross-section view simplified illustration of a drilled bore and notch made in bone taken along broken line Q-Q in FIG. 15B and viewed from a direction indicated by an arrow 1460. As shown in FIG. 16, a leading portion 226 of wing 210-12 is inserted inside notch 1308 and engaged against and gripping at least a portion of a wall 1310 of notch 1308.

Figure 15C:
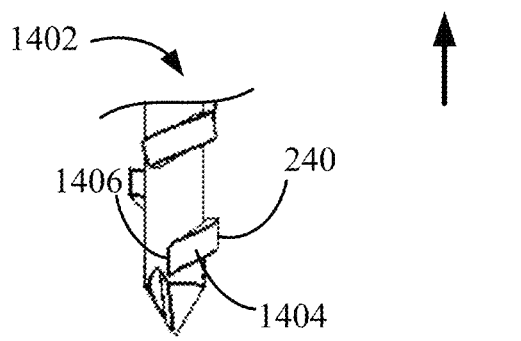
Figure 15D:
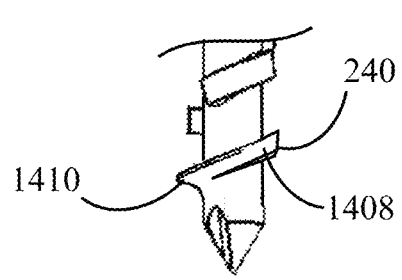

FIGS. 15C and 15D illustrate exemplary embodiments of distal tips of anchors 1402 and 1452 suitable for insertion in notch 1308 and provide anchor 202 with a correct spatial orientation in respect to the surface of cortical bone 525. In the embodiment shown in FIG. 15C, the most distal wing 1404 has hatchet blade geometry comprising a sharp edge 1406 and a trailing surface 240. In the exemplary embodiment depicted in FIG. 15D, bone cutting surface 230 of the most distal wing 1408 has been replaced with a regular cancellous bone thread blade 1410 but maintains trailing surface 240.

Bone Anchor Kit

Figure 17:
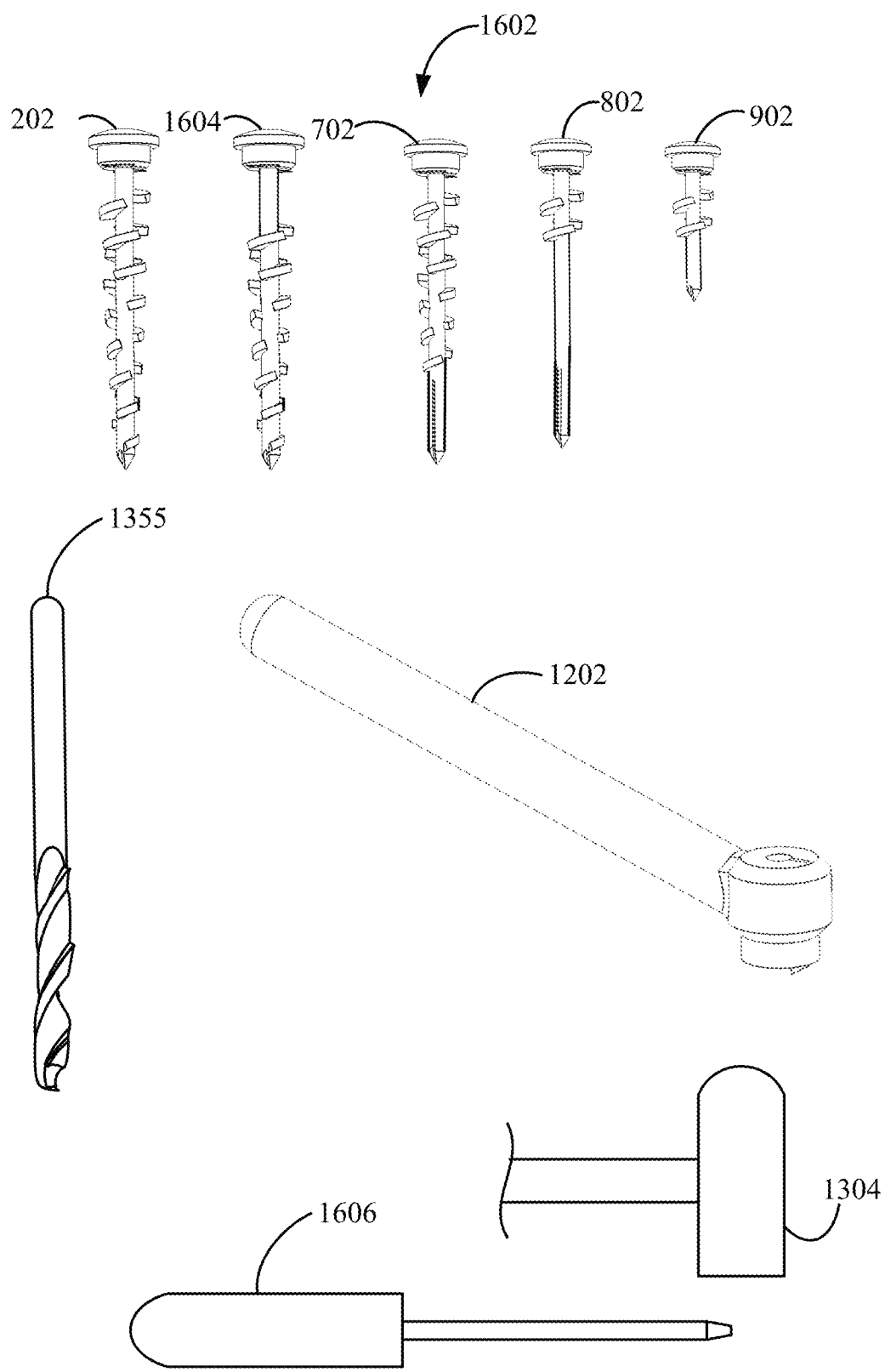
FIG. 17 is a pictorial view and partial diagrammatic view simplified illustration of an embodiment of a bone anchor kit.

In some embodiments and as shown in FIG. 17, which is a pictorial view and partial diagrammatic view simplified illustration of an embodiment of a bone anchor kit, a bone anchor kit 1602 comprises a plurality of bone anchors having varying distances between a distally facing surface 238 of head 206 and a most proximal aspect of the most proximal wing 210 some examples include one or more bone anchors 202, 1604, 702, 802 and/or 902 or any other types of bone anchors as described elsewhere herein, and a bone anchor dedicated drill guide. In some embodiments, bone anchor kit includes one or more drill bits 1355, one or more hammers 1304 and a bone anchor driving tool 1606. In some embodiments, one or more anchors 202, 1604, 702, 802 and/or 902 have heads comprising hexagonal bores sized and fitted to receive a hexagonal screw driver such as that commonly found in orthopedic surgical suites.

A bone anchor kit 1602 can be set for specific orthopedic or dental surgical procedures and contain specific anchors and associated tools for the intended procedure. Such kits may include dental surgical procedure kits, pediatric orthopedic surgical kits, and others. In some embodiments, a bone anchor kit may be combined with other orthopedic surgical kits such as knee resurfacing or total knee replacement kits, hand orthopedic surgery kits, jaw reconstructive surgical kits and similar.

Clawed Bone Plate

Figure 18A:
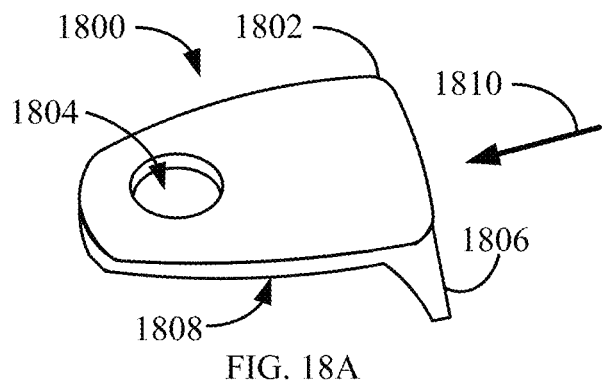
FIGS. 18A, 18B, 18C and 18D are a perspective view and a plan view simplified illustrations of an embodiment of a clawed bone plate in accordance with some embodiments of the invention.
Figure 18B:
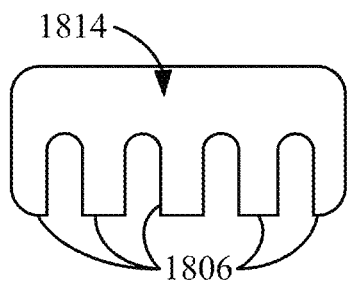
Figure 18C:
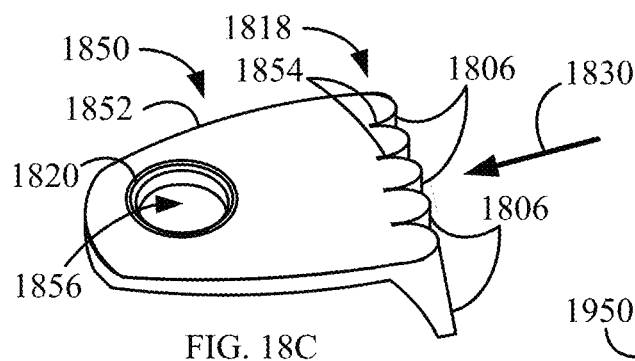

Reference is now made to FIGS. 18A, 18B and 18C, which are perspective view and plan view simplified illustrations of a clawed bone plate to be used with a bone anchor as described elsewhere herein and in accordance with an aspect of some embodiments of the invention.

The rotator cuff is a general term including shoulder complex muscles that predominantly stabilize the glenohumeral joint, but also contribute significantly to movement. The rotator cuff muscles include the Supraspinatus, Infraspinatus, Teres Minor and Subscapularis muscles. The tendons of these muscles coalesce to form the rotator cuff.

Rotator cuff tears are relatively common, and their repair entails surgery to repair a torn tendon in the shoulder. The procedure can be done with a large (open) incision or with shoulder arthroscopy, which uses smaller incisions. The tendons are re-attached to the bone using small rivets (called suture anchors) made of metal or an absorbable material. Sutures are attached to the anchors that tie the tendon back to the bone. Tears in the rotator cuff tendons can be partial or full where the tendon is approximated to the head of the Humerus bone prior to fixation.

In some embodiments, a bone anchor kit e.g., bone anchor kit 1602 comprises a set for specific orthopedic procedures e.g., rotator cuff tendon rupture repair.

In some embodiments, a rotator cuff repair kit is similar to bone anchor kit 1602 as explained elsewhere herein and comprises at least one clawed bone plate 1800 as depicted in FIGS. 18A, 18B, 18C and 18D. FIGS. 18A and 18B are a perspective view and a plan view simplified illustrations of an embodiment of a clawed bone plate in accordance with some embodiments of the invention. FIG. 18B is a plan view of the clawed bone plate in FIG. 18A viewed from a direction indicated by arrow 1810. In some embodiments, clawed bone plate 1800 comprises a generally flat or slightly curved body 1802 having at least one aperture 1804 on one end and one or more claws 1806 on the opposite end. In some embodiments, tips 1822 of claws 1806 are blunt. In some embodiments, tips 1822 of claws 1806 are sharp.

In some embodiments, one or more claws 1806 are angled in respect to body 1802 of clawed bone plate 1800 so that to protrude from a bone-facing surface 1808 of clawed bone plate 1800. In some embodiments, aperture 1804 is sized to accommodate at least a bone anchor 202. In some embodiments, aperture 1804 comprises a step 1820 sized to accommodate at least a shoulder 370 of the bone anchor 202 head 206. In some embodiments, at least two claws 1806 share a common generally flat surface 1814 along before joining body 1802 of clawed bone plate 1800.

Figure 18D:
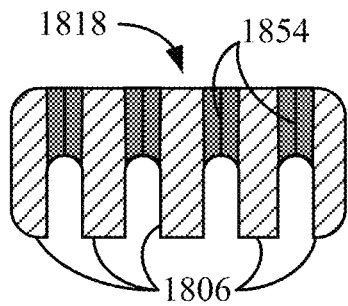

FIGS. 18C and 18D are a perspective view and a plan view simplified illustrations of a clawed bone plate 1850 in accordance with some embodiments of the invention. FIG. 18D is a plan view simplified illustration of clawed bone plate 1850 viewed from a direction indicated by arrow 1830. As shown in FIGS. 18C and 18D, a body 1852 of clawed bone plate 1850 forms clefts 1854 at one end 1818 that define individual claws 1806. In some embodiments, an aperture 1856 at an end of body 1852 opposite to clefted end 1818 comprises a step 1820 sized to accommodate at least a shoulder 370 of the bone anchor 202 head 206.

In some embodiments, clawed bone plate 1800/1850 is made of commonly used bone plate materials such as stainless steel and titanium or any other suitable biocompatible material.

Figure 19A:
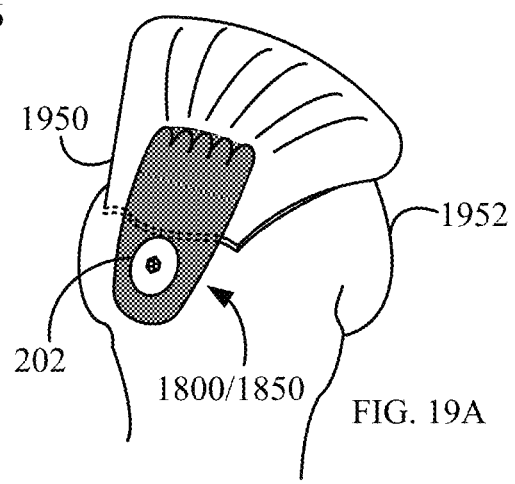
FIGS. 19A, 19B and 19C are a perspective view and a plan view simplified illustrations of implementation of a clawed bone plate in accordance with some embodiments of the invention.
Figure 19B:
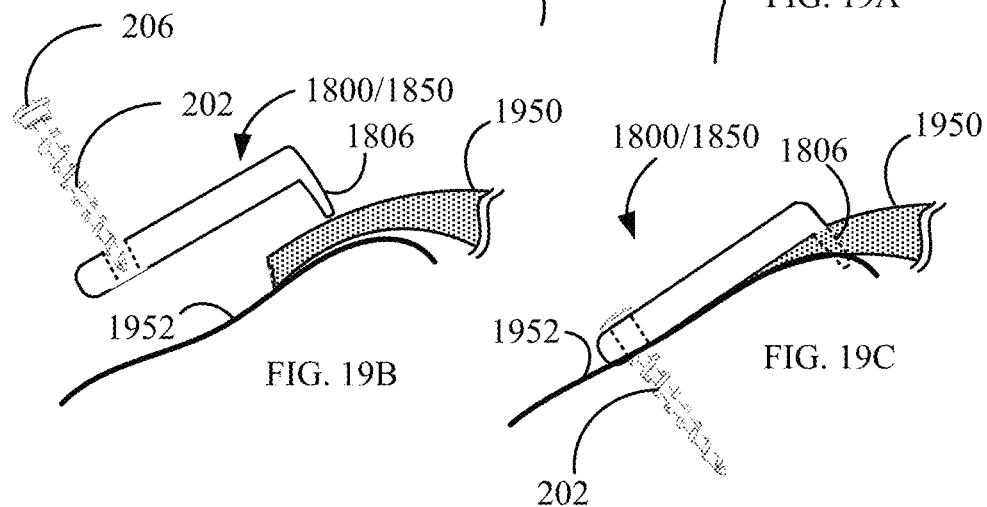
Figure 19C:
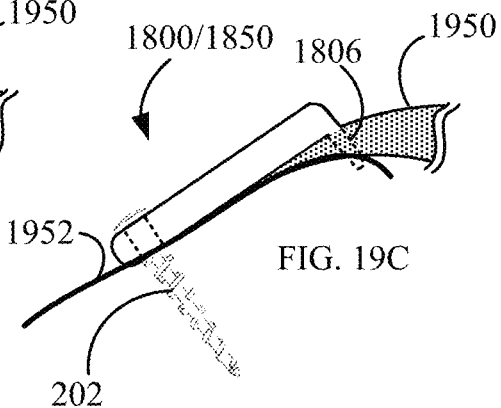

Referring now to FIGS. 19A, 19B and 19C, collectively referred to as FIG. 19, which are a perspective view and side view simplified illustrations of implementation of the clawed bone plate in accordance with some embodiments of the invention. As shown in the exemplary embodiment depicted in FIG. 19, for correction of a partial or full tear of a rotator cuff tendon 1950, clawed bone plate 1800/1850 is applied to the torn tendon so that tips 1822 of individual claws 1806 are in contact with a portion of tendon 1950 extending from a rotator cuff muscle. The aperture 1804/1856 end of clawed bone plate 1800/1850 respectively is positioned over an exposed surface of a head of the Humerus bone 1952. In some embodiments, the torn portion of tendon 1950 is approximated if necessary (e.g., in cases of a full tear).

As shown in the exemplary embodiment depicted in FIG. 19 anchor 202 is driven through aperture 1804/1856 and into the head of the Humerus bone 1952, urging clawed bone plate 1800/1850 against the head of the Humerus bone 1952 and driving claws 1806 into tendon 1950 tissue. In some embodiments, claws 1806 at least partially bite into tendon 1950 and/or surface of the head of the Humerus bone 1952.

A potential advantage in the clawed bone plate 1800/1850 is in that rotator cuff partial or full tear is repaired without the use of sutures and requires only fixation of clawed bone plate 1800/1850 to the head of the Humerus bone 1952 and tendon 1950 using anchor 202.

A potential advantage in the clawed bone plate 1800/1850 is in that the procedure is time sparing and simple to execute.

A Method of Use of a Bone Anchor and a Kit Comprising a Bone Anchor

Figure 20:
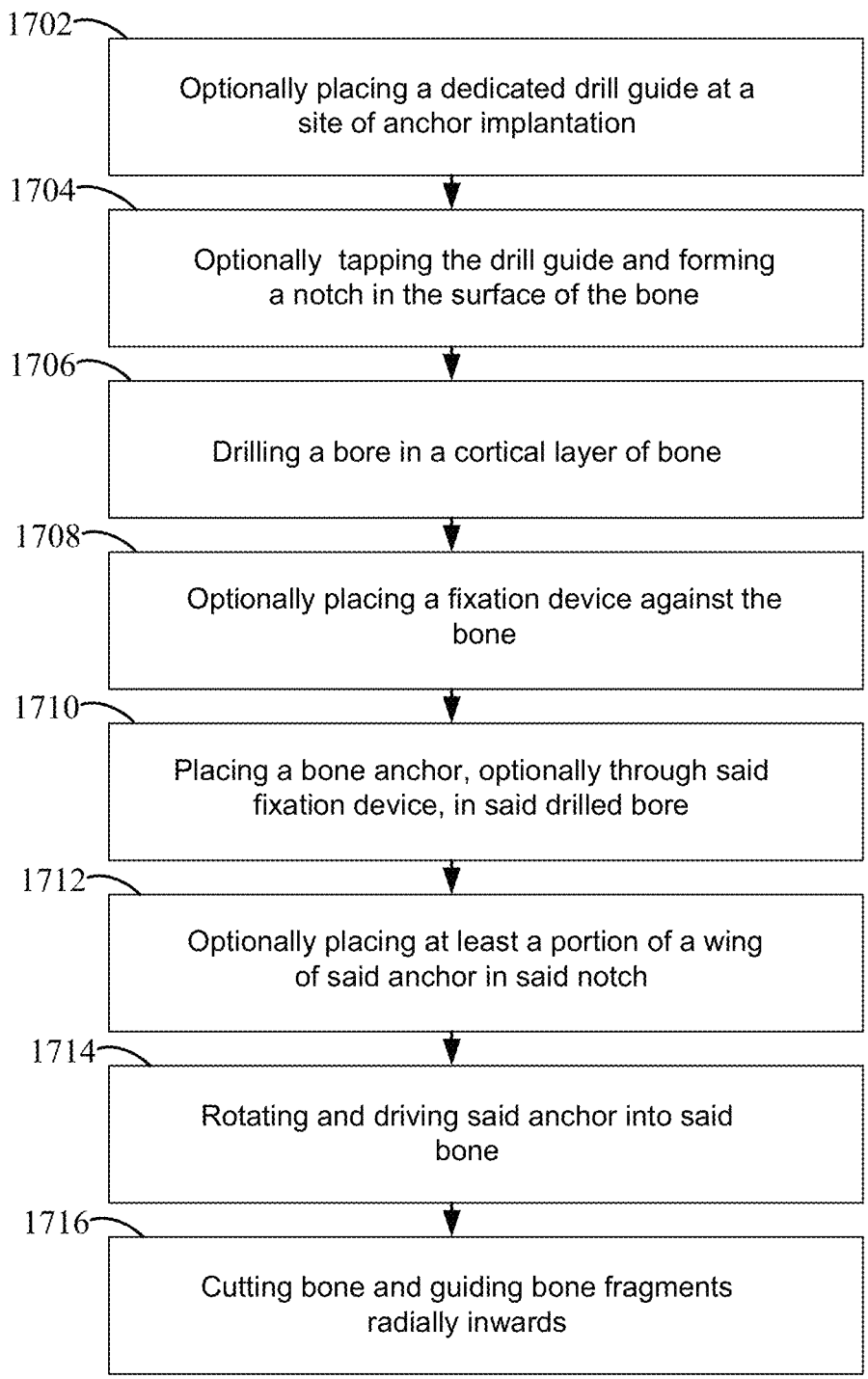
FIG. 20 is a flow chart of an exemplary method of implanting a bone anchor in bone.

Reference is now made to FIG. 20, which is a flow chart of an exemplary method of implanting a bone anchor in bone. In some embodiments, at 1702 the method comprises optionally placing a dedicated drill guide 1202 against surface of a bone at a site of anchor implantation. Optionally, at 1704 tapping drill guide 1202 to form a notch 1308 in surface 1302 of the bone. At 1706 a bore 1306 is drilled in cortical bone layer 525 and a fixation device is optionally placed against the surface 1302 of the bone at 1708. In some embodiments, a fixation device is a bone plate. In some embodiments, a fixation device is a knee resurfacing device or any other suitable device. At 1710 a bone anchor (e.g., anchor 202) is placed in the drilled bore 1306, optionally through an opening in the fixation device. Optionally, at least a portion of a wing 210 is placed in notch 1308 at 1712. At 1714 rotating the bone anchor and collecting at 1716 bone fragments between every two subsequent wings 210 as the anchor is driven deeper into the bone.

The terms "comprises", "comprising", "includes", "including", "has", "having" and their conjugates mean "including but not limited to".

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein, and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A bone anchor comprising:
   an elongated core having a tip at a distal end and coupled to a head at a proximal end; and
   a segmented helical thread defining one or more gaps therein, each gap defining at least a trailing wall, said trailing wall having a cutting surface including at least one cutting edge;
   said bone cutting surface and said cutting edge configured to cut bone and guide bone fragments radially inwards;
   wherein said segmented helical thread comprises wings and said gaps are formed between adjacent consecutive wings and wherein a major radius (r2) of a following second wing is greater at least at said trailing wall than a major radius (r1) of a preceding first wing by at least one dimension (X), expressed by the formula [X=(r2)−(r1)].

2. An anchor according to claim 1, wherein said gap defining at least a leading wall being more distal along said helical thread in respect to said trailing wall.

3. An anchor according to claim 1, wherein each subsequent wing is configured to expand a major radius of a female thread in bone formed by a preceding wing by at least said dimension (X).

4. An anchor according to claim 1, wherein said cutting surface is sized and shaped to, upon rotation of said anchor, push said bone fragments accumulated in said gap along a female thread formed by at least one preceding wing.

5. An anchor according to claim 1, wherein at least one of said cutting edge and said trailing wall is oriented perpendicular to a helix angle of said helical thread.

6. An anchor according to claim 1, wherein said trailing wall is disposed along a plane disposed within 30 degrees from a parallel to a thread axis.

7. An anchor according to claim 1, wherein said trailing wall is concave and arcs radially outwards from said core, along a plane perpendicular to the surface of said trailing wall.

8. An anchor according to claim 1, wherein at least one of said wings comprises a circumferential surface parallel to a longitudinal axis of said core wherein said circumferential surface and said trailing wall meet at said cutting edge.

9. An anchor according to claim 8, wherein said circumferential surface and said trailing wall meet at an angle between 30 and 90 degrees.

10. An anchor according to claim 8, wherein circumferential surfaces of a plurality of wings form an imaginary cone.

11. An anchor according to claim 1, wherein said cutting surface and cutting edge of said trailing wall are disposed along a same radius from said core.

12. An anchor according to claim 1, wherein said cutting surface is arced in respect to a radius of said core such that said cutting edge is disposed more distally along said thread that an edge of said cutting surface attached to said core.

13. An anchor according to claim 1, wherein said trailing wall is angled between 0 and 30 degrees in respect to a radius of said core.

14. A bone anchor kit comprising:
   at least one bone anchor as recited in claim 1;
   at least one bone anchor driving tool; and
   at least one bone anchor dedicated drill guide.

15. A bone anchor kit according to claim 14, wherein said kit further comprises a clawed bone plate for a rotator cuff tear repair.

16. A method for implanting the bone anchor as recited in claim 1 in bone, comprising:
   drilling a bore in a cortical layer of said bone;
   forming a notch in a surface of said bone;
   placing in said bore the bone anchor as recited in claim 1, such that at least a portion of said cutting edge is positioned inside said notch;
   rotating and driving said bone anchor into said bone; and
   cutting bone and guiding bone fragments radially inwards.

* * * * *